US006465495B1

(12) United States Patent
Castelhano et al.

(10) Patent No.: US 6,465,495 B1
(45) Date of Patent: *Oct. 15, 2002

(54) PREPARATION OF PYRIDONE-BASED PHOSPHOTYROSINE MIMETICS AND USES THEREOF

(75) Inventors: Arlindo L. Castelhano, New City, NY (US); Jian-Min Fu, Kalamazoo, MI (US)

(73) Assignee: OSI Pharmaceuticals, Inc., Melville, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/363,877

(22) Filed: Jul. 29, 1999

Related U.S. Application Data

(60) Provisional application No. 60/094,686, filed on Jul. 30, 1998.

(51) Int. Cl.$^7$ .................. C07D 213/02; A61K 31/4412; A61P 35/00

(52) U.S. Cl. ........................ 514/345; 546/141; 546/290; 546/295

(58) Field of Search ................................ 546/141, 290, 546/298, 295; 514/345, 324

(56) References Cited

U.S. PATENT DOCUMENTS

| 4,522,752 A | | 6/1985 | Sisto et al. ............... 260/112.5 |
| 5,342,941 A | * | 8/1994 | Iwasaki et al. .............. 546/301 |

OTHER PUBLICATIONS

Petride et al. Rev Roum. Chim 34(5) 1251–1261, 1989. CA 112:77005, 1990.*
Homma et al. Yakugaku Zasshi 99(6), 588–97, 1979. CA 91:611213, 1979.*
Ball, J.B. and Alewood, P.F., (1990) "Conformational Constraints: Nonpeptide β–Turn Mimics", *Journal of Molecular Recognition* 3:55–64 (Exhibit 2).
Beholz, L.G. et al., (1997) "Formation of Dihydropyridone- and Pyridone–Based Peptide Analogs Through Aza–Annulation of β–Enamino Ester and Amide Substrates with α–Amido Acrylate Derivatives", *The Journal of Organic Chemistry* 62: 1033–1042 (Exhibit 3).
Bernstein, P.R. et al. (1995) "Nonpeptidic Inhibitors of Human Leukocyte Elastase. 6. Design of a Potent, Intratracheally Active, Pyridone–Based Trifluoromethyl Ketone[1]", *Journal of Medicinal Chemistry* 38: 212–215 (Exhibit 4).
Comins, D.L. et al., (1994) "Asymmetric Synthesis of Camptothecin Alkaloids: A Nine–Step Synthesis of (S)—Camptothecin", *Tetrahedron Letters* 35: 5331–5334 (Exhibit 5).

Comins, D.L. et al., (1994) "A Six–Step Synthesis of (±)—Camptothecin", *Journal of Organic Chemistry* 59: 5120–5121 (Exhibit 6).
Curran, D.P. et al., (1992) "New 4+1 Radical Annulations. A Formal Total Synthesis of (±) –Camptothecin", *Journal of the American Chemical Society* 114: 5863–5864 (Exhibit 7).
Hobbs DeWitt et al., (1993) "'Diversomers' : An Approach to Nonpeptide, Nonoligomeric Chemical Diversity", *Proceedings of the National Academy of Sciences* (USA) 90:6909–6913 (Exhibit 8).
Eck, M.J. et al., (1993) "Recognition of a high–affinity phosphotyrosyl peptide by the Src homology–2 domain of p56[lck]", *Nature* 362:87–91 (Exhibit 9).
Farmer, P.S., (1980) "Bridging the Gap Between Bioactive Peptides and Nonpeptides: Some Perspectives in Design", in *Drug Design* ed. E.J. Ariens, (Academic Press, 1980) 10: 119–143 (Exhibit 10).
Freidinger, R.M., (1989) "Non–Peptide Ligands for Peptide Receptors", *Trends in Pharmacological Sciences* 10:270–274 (Exhibit 11).
Houghten et al., (1991) "Generation and Use of Synthetic Peptide Combinatorial Libraries for Basic Research and Drug Discovery", *Nature* 354:84–86 (Exhibit 12).
James, G.L. et al., (1993) "Benzodiazepine Peptidomimetics: Potent Inhibitors of Ras Farnesylation in Animal Cells", *Science* 260:1937–1942 (Exhibit 13).
Jung, M.E. and Starkey, L.S., (1997) "Total Synthesis of (S,S) –Isodityrosine[1]", *Tetrahedron* 53: 8815–8824 (Exhibit 14).
Montserat, J. et al., (1996) "Potent Low Molecular Weight Substrates for Protein–tyrosine Phosphatase", *J. Biol. Chem.* 271:7868–7872 (Exhibit 15).
Morgan, B.A. and Gainor, J.A., (1989) "Approaches to the Discovery of Non–Peptide Ligands for Peptide Receptors and Peptidases", *Annual Reports in Medicinal Chemistry* 24:243–252 (Exhibit 16).
Ohe, T. et al., (1990) "Palladium–Catalyzed Cross–Coupling Reaction of Aryl or Vinylic Triflates with Organoboron Compounds", *Synlett* 4: 221–223 (Exhibit 17).
Plummer, M.S. et al., (1997) "Design, Synthesis, and Cocrystal Structure of a Nonpeptide Src SH2 Domain Ligand", *Journal of Medicinal Chemistry* 40: 3719–3725 (Exhibit 18).

(List continued on next page.)

*Primary Examiner*—Mukund J. Shah
*Assistant Examiner*—Venkataraman Balasubramanian
(74) *Attorney, Agent, or Firm*—John P. White; Cooper & Dunham LLP

(57) ABSTRACT

Novel pyridone mimetics are disclosed which are useful for the treatment of SH2 domain related diseases.

15 Claims, No Drawings

OTHER PUBLICATIONS

Sanderson, P.E.J. et al., (1997) "L–373,890, An Achiral, Noncovalent, Subnanomolar Thrombin Inhibitor," *Bioorganic & Medicinal Chemistry Letters* 7: 1497–1500 (Exhibit 19).

Szardenings, A.K. et al., (1996) "A General and Convenient Synthesis of Novel Phosphotyrosine Mimetics", *Tetrahedron Letters* 37: 3635–3638 (Exhibit 20).

Tamura, S.Y. et al., (1997) "Design and Synthesis of a Novel Class of Thrombin Inhibitors Incorporating Heterocyclic Dipeptide Surrogates", *Bioorganic & Medicinal Chemistry Letters* 7: 1543–1548 (Exhibit 21).

Waksman, G. et al., (1993) "Binding of a High Affinity Phosphotyrosyl Peptide to the Src SH2 Domain: Crystal Structures of the Complexed and Peptide–free Forms", *Cell* 72:779–790 (Exhibit 22).

Homma et al., (1979) *Yakugaku Zasshi* 99(6):588–597 (Abstract only) (Exhibit 24); and.

Petride et al., (1989) *Rev. Roum. Chim* 34(5): 1251–1261 (Abstract only) (Exhibit 25).

* cited by examiner

PREPARATION OF PYRIDONE-BASED PHOSPHOTYROSINE MIMETICS AND USES THEREOF

CROSS REFERENCE TO RELATED APPLICATIONS AND INCORPORATION BY REFERENCE

This application claims the benefit of U.S. Provisional Application No. 60/094,686, filed Jul. 30, 1998, which is hereby incorporated by reference in its entirety. All patents, published patent applications and other references cited throughout this specification are hereby incorporated herein by reference in their entireties.

BACKGROUND OF THE INVENTION

Over the years, mimetics have become immensely important for both organic and medicinal chemists, as well as the pharmaceutical industry due to the multitude of biological active peptides discovered and characterized. For example, peptidomimetics are currently exploited to overcome problems associated with their parent peptides. These improvements include increased selectivity, oral bioavailability and prolonging the activity by hindering enzymatic degradation within the organism.

Cellular signal-transduction pathways that are initiated by transmembrane receptors associating with cytoplasmic protein kinases rely on two small protein domains containing sequences of 50–100 amino acids each. These sequences, referred to as Src homology 2 (SH2) and Src homology 3 (SH3) domains, can fold into modules which interact independently of their surrounding sequences. Because SH2 and SH3 domains are involved in protein-protein interactions in the signal transduction pathway, they represent potential targets for therapeutic drugs. SH2 domains are phosphotyrosine-binding modules found in a variety of important signal-transducing molecules such as nonreceptor tyrosine kinases, phosphatases, and regulatory adapter proteins. Inhibitors that block SH2 domain binding have potential utility in a wide variety of therapeutic areas including metabolic diseases, cancer, inflammation and allergies (Plummer, M. S., el al. *Drug Design and Discovery*, 1996, 13, 75). The high affinity IgE receptor, FcεRI, and associated tyrosine kinases and phosphatase PTP-1C are currently the subject of research (Cambier, J. C., et al. *Annu. Rev. Immunol.*, 1994, 12, 457). Aggregation of this receptor by antigen-antibody complexes leads to the activation of Lyn and Syk with rapid phosphorylation of tyrosine residues in the β- and γ-chain cytoplasmic ITAM (immunoreceptor tyrosine-based activation motif) regions of the receptor. Association of the SH2 domain of syk with the phosphorylated γ-chain of FcεRI in basophils and mast cells leads to downstream activation signals and the allergic response (Kimura, T., et al., *J. Biol. Chem.*, 1996, 271, 27962). The nature of the interaction between SH2 and SH3 domains and proteins has also been the subject of recent study. The three-dimensional structure of SH2 and SH3/peptide complexes have been extensively investigated. These studies revealed that SH2 and SH3 domains interact with protein ligands via hydrophobic contacts on the surface of the domain and protein. These domains have preferences for certain sequences of amino acids, as determined by screening against peptide combinatorial libraries. The protein ligands form a polyproline type II (PPII) left-handed α-helix containing a consensus sequence that can be generalized as XPpXP, where X is an aliphatic amino acid and p is preferably proline to maintain the helix.

All reported naturally-occurring SH2 and SH13 ligands are peptides, although certain non-natural SH2 and SH13 ligands have been described. A variety of mimetics have been described, however, no peptidomimetic has been reported to modulate activity of SH2 or SH3 domains. In one study, a biased combinatorial library was constructed by functionalizing the N-terminus of a pentapeptide with various non-peptide elements, and the constructs were assayed for binding with Src SH3 domain. The non-peptidic moieties appeared to interact with the specificity pocket of Src SH3 domain, lowering the $K_d$ almost 1000-fold from the parent pentapeptide (>1000 mM to 3.4 mM). However, to date, few if any non-peptidic ligands binding in the hydrophobic pockets of SH3 domains have been discovered.

SUMMARY OF THE INVENTION

The present invention is based, at least in part, on the discovery that certain pyridone-based phosphotyrosine mimetics, described infra, can be used to inhibit those disease states associated with protein-protein interactions mediated by a SH2 or a SH3 domain or tyrosine phosphatase. Examples of such disease states include AIDS, an allergy, asthma, anemia, an autoimmune disease, breast cancer, cancer, CML, ALL, erythroleukemias, inflammatory diseases, pre-B-cell leukemia, myelodysplastic syndrome, and osteoporosis. Compositions and methods of the invention include enantiomerically or diastereomerically pure pyridones which, optionally, include amino acid or peptidomimetic residues.

The present invention pertains to compounds represented by the formula (Formula I):

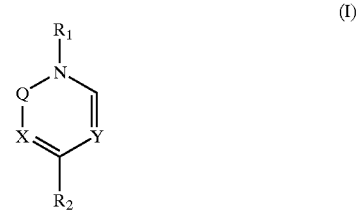

in which

X and Y, each independently, are either CH or N;

Q is either C(O) or forms a single bond between N and X;

$R_1$ is $CHZ_1Z_2$, wherein $Z_1$ and $Z_2$ are each independently, a hydrogen atom, COOH, $PO_3H_2$, or $SO_3H$, provided that both $Z_1$ and $Z_2$ are not both hydrogen atoms, or $CH(OH)Z_1$ or $CHFZ_1$, provided $Z_1$ is not a hydrogen atom; and $R_2$ is a substituted or unsubstituted alkyl, aryl, or alkylaryl moiety or together with X or Y or both X and Y form a substituted or unsubstituted heterocyclic or carbocyclic ring; or a salt or ester thereof Preferably, the salt or ester is a pharmaceutically acceptable salt or ester.

The present invention also pertains to methods for inhibiting a protein-protein interaction mediated by a SH2 domain, a SH3 domain or a tyrosine phosphatase. The method includes contacting the SH2 domain SH3 domain, or the tyrosine phosphatase with a compound represented by Formula I as described above and infra

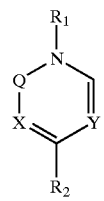
(I)

such that a protein-protein interaction mediated by the SH2 domain, the SH3 domain or tyrosine phosphatase is inhibited.

The invention further pertains to pharmaceutical compositions for inhibiting a protein-protein interaction mediated by a SH2 domain, a SH3 domain or a tyrosine phosphatase in a mammal. The pharmaceutical composition includes a therapeutically effective amount of a compound represented by Formula I as described above and infra

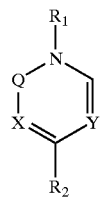
(I)

and a pharmaceutically acceptable carrier.

The present invention is drawn to packaged pharmaceutical composition for inhibiting a protein-protein interaction mediated by a SH2 domain, a SH3 domain or tyrosine phophatase in a mammal. The packaged pharmaceutical composition includes a container holding a therapeutically effective amount of at least one compound represented by Formula I as described above and infra

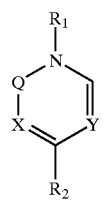
(I)

and instructions for using the compound for treating the protein-protein interaction mediated by the SH2 domain, the SH3 domain or tyrosine phosphatase in a mammal.

The present invention also pertains to methods for the preparation of

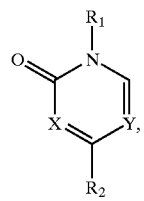

which includes treating

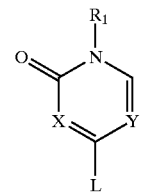

with an alkyl, aryl or alkylaryl alkylating reagent in the presence of a palladium catalyst, to provide

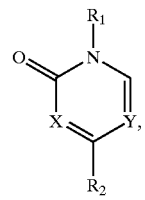

wherein L is a leaving group and wherein X, Y, $R_1$ and $R_2$ are as described above and infra. A preferred leaving group is a triflate and a preferred palladium catalyst is $Pd(PPh_3)_4$.

DETAILED DESCRIPTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on the discovery that certain pyridone-based phosphotyrosine mimetics, described infra, can be used to inhibit those disease states associated with protein-protein interactions mediated by an SH2 or an SH3 domain. Examples of such disease states include AIDS, an allergy, asthma, anemia, an autoimmune disease, breast cancer, cancer, CML, ALL, erythroleukemias, inflammatory diseases, pre-B-cell leukemia, myelodysplastic syndrome, and osteoporosis. Compositions and methods of the invention include enantiomerically or diastereomerically pure pyridones which, optionally, include amino acid or peptidomimetic residues.

The present invention is drawn to compounds represented by the formula (Formula I):

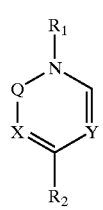
(I)

in which
X and Y, each independently, are either CH or N;
Q is either C(O) is part of a single bond between N and X;
$R_1$ is $CHZ_1Z_2$, wherein $Z_1$ and $Z_2$ are each independently, a hydrogen atom, COOH, $PO_3H_2$, or $SO_3H$, provided that both $Z_1$ and $Z_2$ are not both hydrogen atoms, or $CH(OH)Z_1$ or $CHFZ_1$, provided $Z_1$ is not a hydrogen atom; and $R_2$ is a substituted or unsubstituted alkyl, aryl, or alkylaryl moiety or together with X or Y or both X and Y form a substituted or unsubstituted heterocyclic or carbocyclic ring; or a salt or ester thereof. Preferably, the salt or ester is a pharmaceutically acceptable salt or ester.

In one embodiment, $R_2$ is an aryl moiety or a heteroaryl moiety.

In another embodiment $R_2$ is a methylene group, —$CH_2$—, having attached thereto a substituted or unsubstituted amino acid, peptidomimetic, amine, carbamate, or sulfonamide.

In still another embodiment, $R_2$ is $CH_2NR_3R_4$, wherein $R_3$ and $R_4$ are each independently a hydrogen atom or a substituted or unsubstituted alkyl, aryl, or alkylaryl moiety or together form a substituted or unsubstituted heterocyclic ring, or are each independently $C(O)R_5$, $SO_2R_5$, or $SO_2N(R_5)_2$, wherein $R_5$ is a hydrogen atom or a substituted or unsubstituted alkyl, aryl, or alkylaryl moiety.

In yet another embodiment, $R_2$ is an ethylene group, —$CH_2CH_2$—, having attached thereto a substituted or unsubstituted amino acid, peptidomimetic, amine, carbamate, or sulfonamide.

In another embodiment, $R_2$ is $CH_2CH(COR_6)NR_3R_4$, wherein $R_3$ and $R_4$ are each independently a hydrogen atom or a substituted or unsubstituted alkyl, aryl, or alkylaryl moiety or together form a substituted or unsubstituted heterocyclic ring, or are each independently $C(O)R_5$, $SO_2R_5$ or $SO_2N(R_5)_2$ wherein $R_5$ is a hydrogen atom or a substituted or unsubstituted alkyl, aryl, or alkylaryl moiety and wherein $R_6$ is an amino acid residue, a peptidomimetic or a substituted or unsubstituted alkyl, aryl, or alkylaryl moiety.

In one aspect of the invention the carbocyclic ring formed by $R_2$ and either X or Y or both X and Y can be either aromatic or aliphatic and can have between 4 and 12 carbon atoms, e.g., naphthyl, phenylcyclohexyl, etc., preferably between 5 and 7 carbon atoms, e.g., cyclopentyl or cyclohexyl. Alternatively, $R_2$ and X or Y or both X and Y together can form a heterocyclic ring, such as those disclosed below. Typical heterocyclic rings include between 4 and 12 carbon atoms, preferably between 5 and 7 carbon atoms, and can be either aromatic or aliphatic. The heterocyclic ring can be further substituted, including substitution of one or more carbon atoms of the ring structure with one or more heteroatoms.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamiino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure, even more preferably one to three carbon atoms in its backbone structure. Likewise, "lower alkenyl" and "lower alkynyl" have similar chain lengths. The terms "alkoxyalkyl", "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

As used herein, a "mimetic" of a compound X refers to a compound in which chemical structures of X necessary for functional activity of X have been replaced with other chemical structures that mimic the conformation of X. Examples of peptidomimetics include compounds of the invention including a peptide portion in which the peptide backbone is substituted with one or more benzodiazepine molecules (see e.g., James, G. L. et al., (1993) Science 260:1937–1942) and "retro-inverso" peptides (see U.S. Pat. No. 4,522,752 by Sisto), described further below. A "residue" refers to an amino acid or amino acid mimetic incorporated in the peptide by an amide bond or amide bond mimetic. Approaches to designing peptide derivatives, analogs and mimetics are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med Chem.* 24:243; and Freidinger, R. M. (1989) *Trends Pharmacol. Sci.* 10:270.

An "amino acid mimetic" refers to a moiety, other than a naturally occurring amino acid, that conformationally and functionally serves as a substitute for a particular amino acid in a peptide-containing compound without adversely interfering to a significant extent with the function of the protease (e.g., inactivation of elastase). In some circumstances, substitution with an amino acid mimetic may actually enhance properties of the inhibitor (e.g., interaction of the compound of the invention with an SH2 domain). Examples of amino acid mimetics include D-amino acids. Peptides substituted with one or more D-amino acids may be made using well known peptide synthesis procedures. The effect of amino acid substitutions with D-amino acids and other peptidomimetics can be tested using assays as described infra.

The compounds of the invention include isosteres. The term "isostere" as used herein refers to amino acids that can be substituted in the compound's backbone because of similar or equivalent steric conformations. The term specifically includes peptide backbone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[C(S)NH$_2$], ψ[NHCO], ψ[C(O)CH$_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al.(993) *Science* 260:1937–1942)

Other possible modifications include an N-alkyl (or aryl) substitution (ψ[CONR]), backbone crosslinking to construct lactams and other cyclic structures, or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent compound includes Ala-Tyr, the retro modified form is Tyr-Ala, the inverso form is ala-tyr, and the retro-inverso form is ala-thr (lower case letters refer to D-amino acids). Compared to the parent compound, a retro-inverso peptide has a reversed backbone while retaining substantially the original spatial conformation of the side chains, resulting in a retro-inverso isomer with a topology that closely resembles the parent peptide and is able to bind the selected cysteine protease. See Goodman et al. "*Perspectives in Peptide Chemistry*" pp. 283–294 (1981). See also U.S. Pat. No. 4,522,752 by Sisto for further description of "retro-inverso" peptides.

The term "amino-derivative group" is intended to include amino-terminal modifications of the peptide-containing compounds of the invention. Examples of N-terminal modifications include alkyl, cycloalkyl, aryl, aralkyl, and acyl groups. A preferred N-terminal modification is acylation. Preferred N-terminal acyl or acyloxy groups include acetyl (denoted Ac), and benzoyl, as well as acyloxy groups such as methoxycarbonyl, t-butoxycarbonyl and benzyloxycarbonyl (also denoted "Cbz"). The N-terminal residue may be linked to a variety of moieties other than amino acids such as polyethylene glycols (such as tetraethylene glycol carboxylic acid monomethyl ether), pyroglutamic acid, succinoyl, methoxy succinoyl, benzoyl, phenylacetyl, 2-, 3-, or 4-pyridylalkanoyl, aroyl, alkanoyl (including acetyl and cycloalkanoyl e.g., cyclohexylpropanoyl), arylalkanoyl, arylaminocarbonyl, alkylaminocarbonyl, cycloalkylaminocarbonyl, alkyloxycarbonyl (carbamate caps), and cycloalkoxycarbonyl, among others.

Except as otherwise noted, standard abbreviations are used throughout this disclosure when describing peptide substituents of the compounds of the invention.

The term "pyridone" is art recognized and is intended to include those compounds having the general formula

existing in tautomeric form.

The term "pyrazole" is art recognized and is intended to include those compounds having the general formula

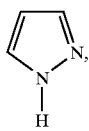

e.g those compounds of the invention where Q is part of a single bond between N and X.

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

Another aspect of the present invention pertain to methods for the preparation of

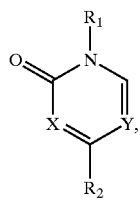

treating

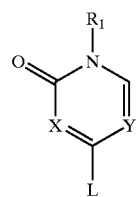

with an alkyl, aryl or alkylaryl alkylating reagent in the presence of a palladium catalyst, to provide

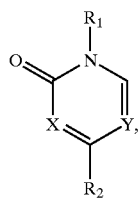

wherein L is a leaving group and wherein

X and Y, each independently, are either CH or N;

$R_1$ is $CHZ_1Z_2$, wherein $Z_1$ and $Z_2$ are each independently, a hydrogen atom, COOH, $PO_3H_2$, or $SO_3H$, provided that both $Z_1$ and $Z_2$ are not both hydrogen atoms, or $CH(OH)Z_1$ or $CHFZ_1$, provided $Z_1$ is not a hydrogen atom; and $R_2$ is a substituted or unsubstituted alkyl, aryl, or alkylaryl moiety or together with X or Y or both X and Y form a substituted or unsubstituted heterocyclic or carbocyclic ring or a salt or ester thereof A preferred leaving group is a triflate. A preferred palladium catalyst is $Pd(PPh_3)_4$.

The compounds of the invention can be prepared by the methods described herein, or by other methods which will be routine for the ordinarily skilled artisan in light of the teachings herein. For example, the compounds of the invention can be prepared from chiral or non-chiral starting materials, and can be enantiomerically pure or a racemic mixture of compounds. Although the syntheses described produce a racemic modification (e.g., racemization occurs at the alkylation step), enantiomeric purity can be retained through the alkylation step by means of "self-reproduction" of chirality (see, e.g., Seebach, D. et al., *J. Am. Chem. Soc.* (1983) 105:5390–5398). Alternatively, chiral auxiliaries or catalysts can be employed to obtain enantiomerically enriched products. Enantiomers can also be separated by resolution techniques, such as chiral chromatography or the use of chiral acids or bases, as are conventional in the art.

Furthermore, analogs and derivatives of the compounds of the invention can be prepared by standard synthetic methodologies in light of the herein.

Among heteroaromatic compounds, substituted pyridones have been found as important starting materials for the synthesis of more complex molecules (Scriven, E. F. V. *Comprehensive Heterocyclic Chemistry;* Katritzky, A. R. and Rees, C. W., Eds., Vol. 2, Pergamon Press, 1984; Comins, D. L.; Gao, J. *Tetrahedron Lett.* 1994, 35, 2819; Sieburth, S. M. et al., *J. Org. Chem.* 1994, 59, 80; Schmidhauser, J. C.; Khouri, F. F. *Tetrahedron Lett.* 1993, 34, 6685; and Sieburth, S. M.; Chen, J.-L. *J. Am. Chem. Soc.* 1991, 113, 8163). The pyridone structure also appears in a number of natural products such as camptothecin, and as a peptidomimetic element in enzyme inhibitors of elastase and thrombin(Comins, D. L. et al., *J. Org. Chem.,* 1994, 59, 5120; Comins, D. L. et al., *Tetrahedron Lett.* 1994, 35, 5331; Curran, D. P. et al. *J. Am. Chem. Soc.,* 1992, 114, 5863; Beholz, L. G. et al., *J. Org. Chem.* 1997, 62, 1033; Bernstein, P. R. et al. *J. Med. Chem.,* 1995, 38, 212; Sanderson, P. E. J. et al. *Bioorg. & Med. Chem. Lett.* 1997, 7, 1497; Tamura, S. Y. et al. *Bioorg. & Med. Chem. Lett.* 1997, 7, 1543). The pyridone N-substituent introduces an element of diversity or a site for further modification via library synthesis. In the specific case of the N-phosphonomethyl moiety, 4a, (Scheme 1) this results in a phosphotyrosine mimetic, a key component in ligands recognized by protein SH2 domains implicated in cancer, inflammation and allergy.

An efficient synthesis of N-,4-disubstituted pyridones through palladium catalyzed cross coupling reactions of N-alkyl pyridone triflates 4a–c (Scheme 1, below) with aryl boronic acids or the zinc reagent of β-iodoalanine. Coupling conditions are described that render pyridone triflates useful in reactions with a variety of aryl, heteroaryl, alkynyl, and alkyl coupling partners at or near room temperature. The pyridone triflates were made by regiospecific N-alkylation of commercial O-benzylpyridone 1 with potassium carbonate in acetonitrile (Scheme 1). Hydrogenolysis with Pd—C in methanol generated N-alkyl-4-hydroxypyridones 3a–c. The formation of triflates 4a–c occurred rapidly at −78° C. with triflic anhydride and triethylamine.

Scheme 1

(i) $K_2CO_3$, $CH_3CN$, $R_1X$, reflux, 2d
(ii) $H_2$, Pd—C, MeOH, rt, 2h
(iii) $Et_3N$, $(CF_3SO_2)_2O$, $CH_2Cl_2$, -78° C., 5 min R = Bn  2 ⎱ ii
R = H   3 ⎰ iii
R = $SO_2CF_3$ 4

| | $R_1$-X | Yield (%) | | |
|---|---|---|---|---|
| | | 2 | 3 | 4 |
| a | $BrCH_2P(O)(OPr^i)_2$ | 98 | 96 | 70 |
| b | $BrCH_2COOBu^t$ | 86 | 86 | 67 |
| c | $Cl(CH_2)_3COOMe$ | 68 | 100 | 67 | aryl boronic acids and phenyl acetylene (Table 1). Although the Suzuki reaction is normally carried out at reflux temperatures, several groups have reported the coupling of organobromo and iodo reagents with aryl boronic acids at ambient temperature (Kang, S-K. et al., *J. Org. Chem.*, 1996, 61, 9082; Anderson, J. C. et al., *Synlett*, 1995, 765; Genet, J. P. et al., *Tetrahedron Lett.*, 1995, 36, 1443; Campi, E. M. et al., *J. Chem. Soc. Chem. Commun.* 994, 2395; Genet, J. P., et al. *Synlett*, 1992, 715). However, the corresponding non-queous coupling between aryl triflates and boronic acids do not appear to have been reported (Ohe, T. et al., *Synlett*, 1990, 221; Hoshino, Y. et al. *Bull. Chem. Soc. Jpn.*, 988, 61, 3008). Such conditions are preferred for robotic synthesis of compound libraries for drug screening.

Indeed, coupling of 4 with 2-thienyl boronic acid was found to proceed at room temperature under the specific conditions of $Pd(PPh_3)_4/K_2CO_3$/THF-DMA (1:1) in a superior yield (96%) than the regular reflux conditions $Pd(PPh_3)_4$/aq $NA_2CO_3$/DME), (entries 4 and 5, Table 1).

TABLE 1 a $R_1 = CH_2P(O)(OPr^i)_2$
b $R_1 = CH_2COOBu^t$
c $R_1 = (CH_2)_3COOMe$

Palladium catalyzed triflate coupling reactions

| Entry | Y | Product | Catalyst | Reactions conditions | Yield (%) |
|---|---|---|---|---|---|
| 1 | Ph | 6a | $Pd(PPh_3)_4$ | 90° C./aq $Na_2CO_3$/DME | 64 |
| 2 | 2-MePh | 7a | $Pd(PPh_3)_4$ | 90° C./aq $Na_2CO_3$/DME | 91 |
| 3 | 3-$NO_2$Ph | 8a | $Pd(PPh_3)_4$ | 90° C./aq $Na_2CO_3$/DME | 81 |
| 4 | 2-thienyl | 9a | $Pd(PPh_3)_4$ | 90° C./aq $Na_2CO_3$/DME | 78 |
| 5 | 2-thienyl | 9a | $Pd(PPh_3)_4$ | 25° C./$K_2CO_3$/THF-DMA | 96 |
| 6 | —Ph | 10b | $PdCl_2(PPh_3)_2$ | 100° C./$iPr_2NEt$/DMF | 94 |
| 7 | —Ph | 11c | $PdCl_2(PPh_3)_2$ | 100° C./$iPr_2NEt$/DMF | 74 |

The palladium catalyzed cross coupling reaction has been widely used in organic synthesis for the construction of a variety of complex molecules (Suzuki, A. *Chem. Rev.*, 1995, 95, 2457; Sneickus, V. *Chem. Rev.* 1990, 90, 879; Stille, J. K. *Agnew. Chem. Int. Ed. Engl.* 1986, 25, 508). Organo triflates have been reported to couple with tin, boron, zinc and Grignard reagents (Echavarren, A. M. et al. *J. Am. Chem. Soc.*, 1987, 119, 5487; Suzuki, A. *J. Org. Chem.* 1993, 58, 2201; Fu, J-M, et al., *Tetrahedron Lett.* 1990, 31, 1665; Huth, A. et al., *Tetrahedron Lett.*, 1989, 45, 6679; Superchi, S. et al., *Tetrahedron Lett.* 1996, 37, 6057; Quesnelle, C. A. et al. *Synlett*, 1994, 349; Arcadi, A. et al., *Synlett*, 1990, 47; Sengupta, S. et al. *J. Org. Chem.* 1992, 57, 4066). The pyridone triflate 4 was successfully coupled with Accordingly, room temperature conditions were applied to the coupling of 4 with other boronic acids (Scheme 2). As a preamble to robotic synthesis, cross coupling reactions were carried out in 20 ml borosilicated vials by mixing triflate 4a with commercial boronic acids, palladium catalyst, and potassium carbonate in 1:1 ratio of THF and DMA. The mixture was shaken on a J-CHEM shaker for 48 h. To assure purity, the mixture was filtered and the crude product purified by preparative thin layer chromatography. Monosubstituted phenyl boronic acids with electron donating and electron withdrawing groups at ortho-, meta-, or para positions did not affect the outcome of the product. Disubstituted phenyl, naphthyl, and heteroaromatic boronic acids also gave excellent yields of coupled product. The isopropyl phosphonate esters were further hydrolyzed with iodo-trimethylsilane and N,O-bis(trimethylsilyl)acetamide in acetonitrile, followed by TFA/CH$_3$CN/H$_2$O to yield the corresponding phosphonic acids (Szardenings, A. K. et al., *Tetrahedron Lett.*, 1996, 37, 3635; Montserat, J. et al., *J. Biol. Chem.* 1996, 271, 7868).

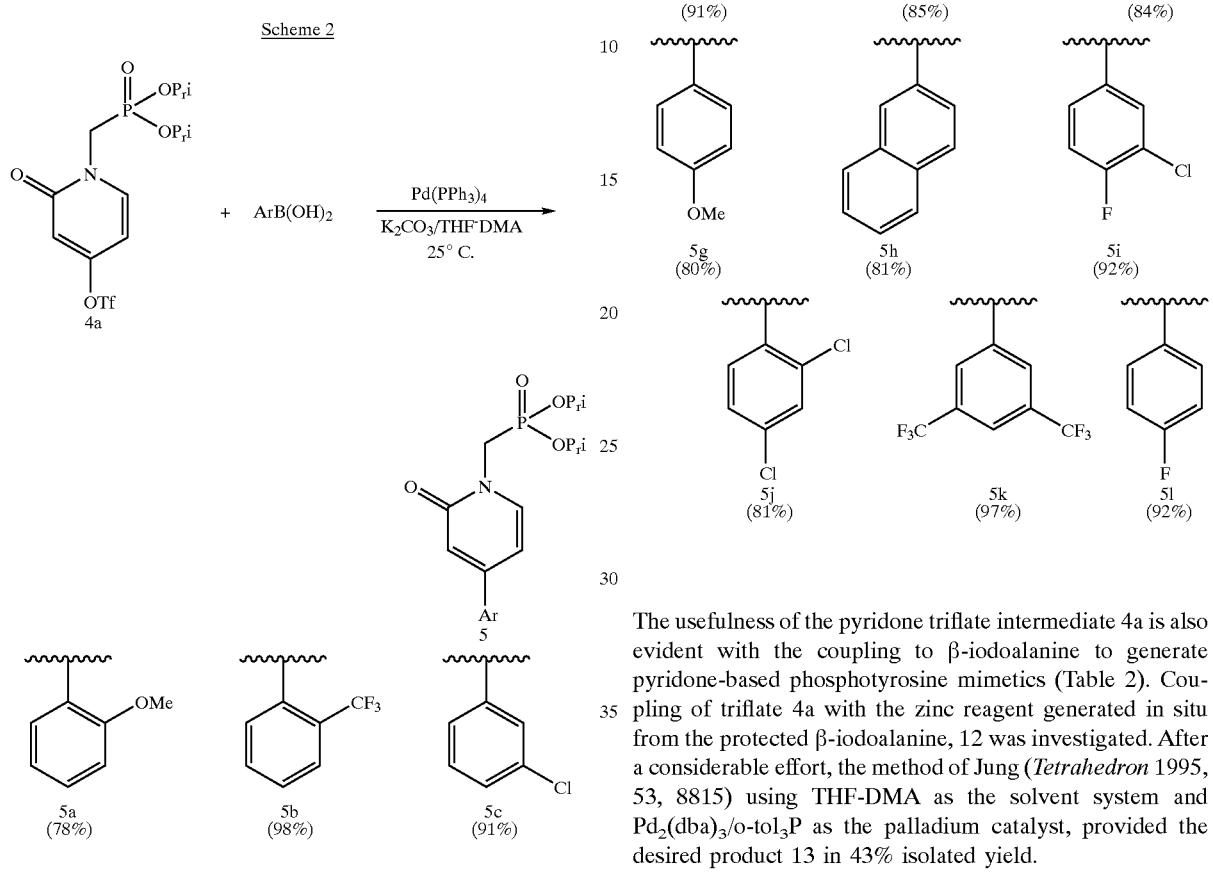

The usefulness of the pyridone triflate intermediate 4a is also evident with the coupling to β-iodoalanine to generate pyridone-based phosphotyrosine mimetics (Table 2). Coupling of triflate 4a with the zinc reagent generated in situ from the protected β-iodoalanine, 12 was investigated. After a considerable effort, the method of Jung (*Tetrahedron* 1995, 53, 8815) using THF-DMA as the solvent system and Pd$_2$(dba)$_3$/o-tol$_3$P as the palladium catalyst, provided the desired product 13 in 43% isolated yield.

TABLE 2

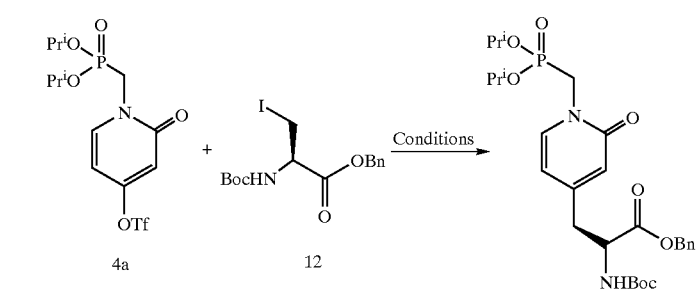

| Entry | Zn Reagent | Palladium Catalyst | Solvent | Temp. | Yield (%) |
|---|---|---|---|---|---|
| 1 | Zn—Cu/sonication | PdCl$_2$(PPh$_3$)$_2$ | PhH-DMA | sonication | 0 |
| 2 | Zn—Cu/sonication | Pd(PPh$_3$)$_4$ | PhH-DMA | sonication | 0 |
| 3 | Zn dust | PdCl$_2$(o-tol$_3$P)$_2$ | THF-DMA | 55° C. | 7 |
| 4 | Zn dust | Pd(PPh$_3$)$_4$ | THF-DMA | 55° C. | 15 |
| 5 | Zn dust | Pd$_2$(dba)$_3$/dppf | THF-DMA | 55° C. | 0 |
| 6 | Zn dust | Pd$_2$(dba)$_3$/P(2-furyl)$_3$ | THF-DMA | 55° C. | 14 |
| 7 | Zn dust | Pd$_2$(dba)$_3$CHCl$_3$/o-tol$_3$P | THF-DMA | 55° C. | 21 |
| 8 | Zn dust | Pd$_2$(dba)$_3$/AsPh$_3$ | THF-DMA | 55° C. | 25 |
| 9 | Zn dust | Pd$_2$(dba)$_3$/o-tol$_3$P | THF-DMA | 55° C. | 43 |

The N-alkyl, 4-pyridone triflate 4 is a versatile reagent for palladium catalyzed cross coupling reactions with phenyl acetylene (sp carbon) and aryl boronic acids ($sp^2$ carbon) at room temperature, and the zinc reagent of β-iodoalanine ($sp^3$ carbon).

Structural detail provided from X-ray and NMR studies of high affinity pTyr containing peptides has guided the design of SH2-directed ligands (Plummer, M. S. et al. *J. Med. Chem.,* 1997, 40, 3719). Selective ligands for Sh2 domains containing pTyr or phosphate-resistant pTyr analogs and pseudo-peptidic elements, have been developed for SH2 domains of pp60$^{c-src}$, p85 subunit of PI-3 kinase, and other proteins (Domchek, S. M., et al. *Biochemistry,* 1992, 31, 9865; Plummer, M. S. et al., *Bioorg. & Med. Chem. Lett.* 1997, 5, 41; Furet, P. et al., *J. Med. Chem,* 1997, 40, 3551; Revesz, L. et al. *Bioorg. & Med. Chem. Lett.,* 1997, 7, 2875). Ligand studies with (phosphonomethyl) phenylalanine (Pmp), wherein the phosphate ester oxygen (>COPO$_3$H$_2$) has been replaced by a methylene unit (>CH$_2$PO$_3$H$_2$) and Pmp analogs bearing fluorine or hydroxyl, indicate a $pK_{A2}$ requirement (pTyr $pK_{A2}$=5.7 vs. Pmp $pK_{A2}$=7.1) and an H-bond to the phosphate ester oxygen (Burke, J. et al. *Biochemistry,* 1994, 33, 6490; Burke, J. et al., *Tetrahedron Lett.,* 1993, 34, 4125; Liu, W. et al., *Tetrahedron Lett.,* 1997, 38, 1389; Chen, L. et al. *Biochem. Biophys. Res. Comm.* 1995, 216, 976). It was thought that the inductive effect of a heterocycle on phosphonate acidity, (Het-CH$_2$PO$_3$H$_2$), would result in a $pK_{A2}$ close to that of pTyr. As indicated in Scheme 3, the pyridone methylphosphonate moiety was expected to maintain ionic and H-bonding interactions observed in phosphate-based ligands (Waksman, G. et al. *Cell,* 1993, 72, 779; Eck, M. J. et al., *Nature,* 1993, 362, 87).

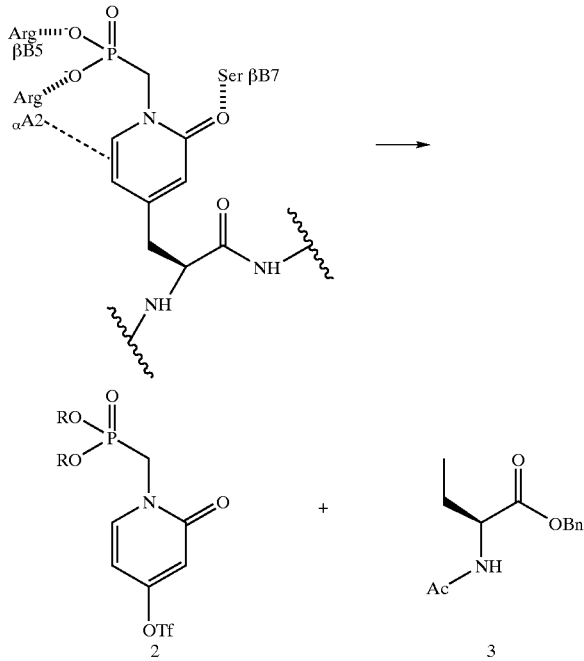

The first approach in preparing the key pyridone pTyr mimetic began with commercial (4-pyridinyl)alanine. Because pyridine to pyridone conversion has been reported for simple systems, rearrangement of N$^α$-Boc-(4-pyridinyl-N-oxide)alanine benzyl ester to the corresponding (4-pyridone)alanine with acetic anhydride was investigated (Scheme 4) (Kelly, T. R. et al. *J. Am. Chem. Soc.,* 1990, 119, 8024). The presence of 5 in crude product was established by MS but the yield was low and pure material was elusive.

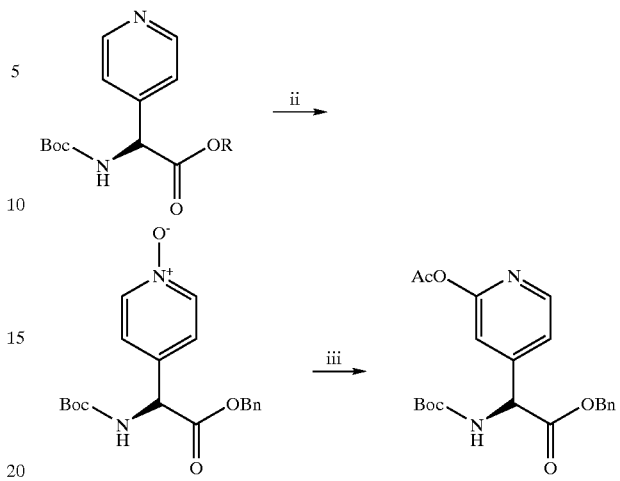

Alternatively, the palladium catalyzed cross coupling of triflate 2, already possessing the phosphonate moiety, and β-iodoalanine 3 appeared to be a feasible, convergent synthesis of 6 (Scheme 4) (Smyth, M. S., et al. *Tetrahedron Lett.,* 1994, 35, 551; Walker, M. A. et al., *Synlett.,* 1997, 169). Starting with commercial 4-(O-benzyl)pyridone, alkylation with BrCH$_2$P(O)O$^i$Pr)$_2$ and K$_2$CO$_3$ in acetonitrile at reflux gave N-alkylated product in 98% yield. The benzyl group of the phosphonomethylpyridone intermediate was then removed by hydrogenolysis in 96% isolated yield. The triflate moiety was introduced with triflic anhydride and triethylamine at −78° C. for 5 min in about 70% isolated yield, longer reaction time led to lower yields of triflate product. Palladium catalyzed coupling of 2 with the zinc reagent of β-iodoalanine, prepared according to Jung (Jung, M. E. and Starkey, L. S., *Tetrahedron* 53: 8815 (1995)), Pd$_2$(dba)$_3$/o-tol$_3$P at 55° C., provided the desired product 6 reproducibly in 43% yield. Investigation of other palladium reagents did not lead to an improvement in yield. Assembly of a pyridone-based ligand with recognition for SH2 domains involved the additional condensation of 6 with the peptidomimetic 7, an entity developed for the P+1 to P+3 pockets, and N$^α$-acetylation of the N-terminus (Eaton, S. R. et al. "Peptidomimetic inhibitors of the association of platelet derived growth factor-β receptor with phosphatidylinositiol 3-kinase", 25$^{th}$ National Medicinal Chemistry Symposium, Ann Arbor, Mich., Poster #2). Thus, treatment of 6 with TFA and acetylation with acetic anhydride proceeded in 76% yield for the two-step transformation. Hydrogenolysis with H$_2$/Pd(OH)$_2$/EtOAc gave the carboxylic acid 10 in 94% yield. Compound 10: m.p. $^1$H NMR (200 MHz, CDCl$_3$) δ 1.21 (s, 3H, OCH(CH$_3$)$_2$), 1.24 (s, 3H, 10CH(CH$_3$)), 1.28 (s, 3H, OCH(CH$_3$)$_2$), 1.31 (s, 3H, OCH(CH$_3$)$_2$), 1.43 (s, 9H, OC(CH$_3$)$_3$), 2.94–3.02 (m, 2H, (CHCHCOOH), 4.28–4.75 (m, 5H, 2×OCH(CH$_3$)$_2$), N—CH$_2$, CH$_2$CHCOOH), 5.40 (br, 1H, NH), 6.26–6.29 (d, J=6.6 Hz, 1H, ArH), 7.43–7.46 (d, J=6.6 Hz, ArH). $^{13}$C NMR (50.3 MHz, CDCl3) δ.

Coupling of 10 with ValAla dibutyl amide 7, afforded 11 as a single isomer revealing sterochemical integrity in the palladium coupling step. Unmasking of the phosphatase isopropyl esters with typical conditions for ethyl phosphate esters, namely iodotrimethylsilane and N,O-bis (trimethysilyl) acetamide, led to the oxazole 12 in 51% isolated yield (Szardenings, A. K. et al., *Tetrahedron Lett.,* 1996, 37, 3635). To avoid this intramolecular cyclization and dehydration of the acetamide moiety, the N-acetyl group would need to be introduced after phosphonate ester hydrolysis. This was achieved by first coupling N-Boc acid 8 with 7 (EDCI/HOBT) to give 13 in 85% yield. Treatment of 13 with bromotrimethylsilane in acetonitrile and subsequently aqueous acetone resulted in isopropyl ester hydrolysis and Boc removal. Acetylation of the zwitterionic intermediate 14 with $Ac_2O$ gave the desired target compound 15 as a single isomer as determined by $^1H$ and $^{13}C$ NMR analysis. Compound 15: m.p. $^1H$ NMR (200 MHz, $CDCl_3$) δ0.84–0.95 (m, 12H, 2xNCH$_2$CH$_2$CH$_2$CH$_3$, 2xOCH (CH$_3$)$_2$), 1.17–1.55 (m, 31H), 2.01–2.13 (m, 2H), 2.14–3.29 (m, 6H), 3.37–3.52 (m, 2H), 4.28–4.41 (m, 4H), 4.57–4.85 (m, 4H), 5.4–5.50 (d, J=8 Hz, 1H), 6.13–6.17 (d, J=8 Hz, 1H), 6.43 (s, 1H), 6.92–6.96 (d, J=8 Hz, 1H), 7.19–7.23 (d, J=8 Hz, 1H), 7.38–7.42 (d, J=8 Hz, 1H).

The corresponding phosphate 16 (reported to block the association of PDGF-β receptor with p85 C-SH2; $IC_{50}$= 0.077 μM) was also assembled for comparative biochemical evaluation. BiaCore analysis of 15 showed 50% inhibition of binding of the p85 N-terminal SH2 domain to a CD19 phosphopeptide at 50 μM. By comparison, the canonical phosphopeptide 16 exhibited 98% inhibition at 20 μM.

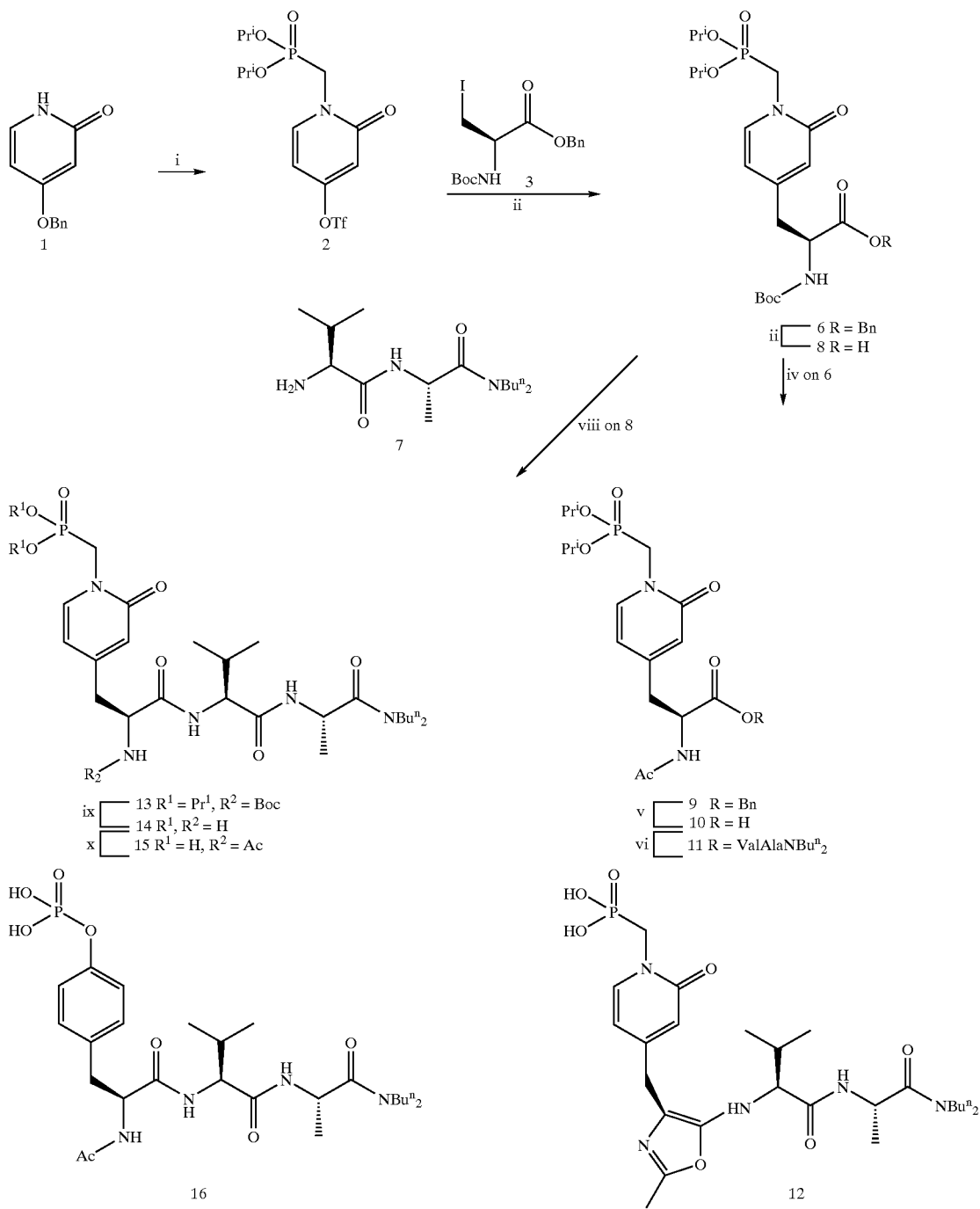

Results from SH2 domain binding assays for several compounds synthesized by the methods of the invention are given in the Table 3.

such that a protein-protein interaction mediated by the SH2 domain, the SH3 domain or tyrosine phosphatase is inhibited.

TABLE 3

SH2 Assay

| Compound | Assay Conc. ($\mu$M) | Inhibition |
|---|---|---|
| 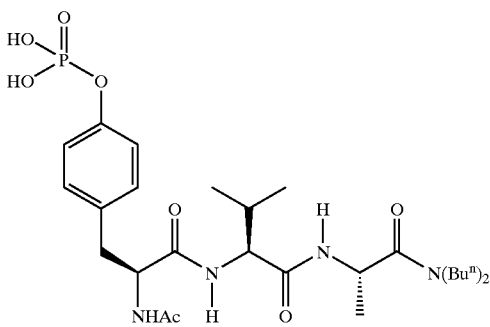 | 20 | 98% |
| 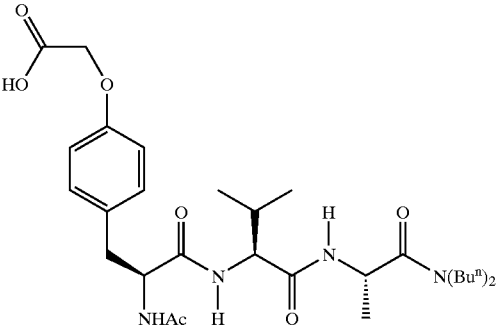 | 20<br>100<br>500 | 19%<br>25%<br>50% |
| 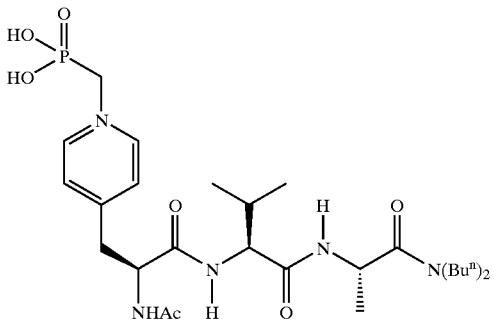 | 50 | 50% |

Another aspect of the present invention pertains to methods for inhibiting a protein-protein interaction mediated by a SH2 domain, a SH3 domain or a tyrosine phosphatase. The method includes contacting the SH2 domain, SH3 domain, or the tyrosine phosphatase with a compound represented by Formula I, as described above,

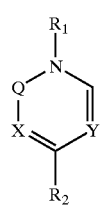

(I)

Protein tyrosine kinases play a role in signal transduction through phosphorylation of substrate proteins as well as corresponding recognition and binding of other phosphoproteins (Schlessinger, J., Ulirich, A., Growth Factor Signaling by Receptor Tyrosine Kinases, *Neuron* 1992, 9, 383–391) (Schlessinger, J., Ulrich, A., Signal Transduction by Receptors with Tyrosine Kinase Activity, *Cell* 1990, 61, 203–212). The prototypical nonreceptor tyrosine kinase pp60$^{c-src}$ contains a catalytic kinase region, the SH1 (src homology 1) domain, which is highly conserved among members of the src family, an SH2 (src homology 2) domain (Margolis, B., Proteins with SH2 Domains: Transducers in the Tyrosine Kinase Signaling Pathway, *Cell Growth Differ.* 1992, 3, 73–80) (Koch, A. C., et al., SH2 and SH3 Domains: Elements that Control Interactions of Cytoplasmic Signaling Proteins, *Science* 1991, 252, 668–674) that binds phosphotyrosine-containing proteins, and an SH3 (src homology 3) domain (Margolis, B., Proteins with SH2

Domains: Transducers in the Tyrosine Kinase Signaling Pathway, *Cell Growth Differ.* 1992, 3, 763–80) (Koch, A. C., et al., SH2 and SH3 Domains: Elements that Control Interactions of Cytoplasmic Signaling Proteins, *Science* 1991, 252, 668–674) that recognizes proline-rich sequences (Pawson, T., Schlessinger, J., SH2 and SH3 Domains, *Curr. Biol.* 1993, 3, 434–442). Overexpression or hyperactivation of pp60$^{c\text{-}src}$ has been implicated in the development of human colon and breast carcinomas (Schlessinger, J.; Ullrich, A. Growth Factor Signaling by Receptor Tyrosine Kinases, *Neuron* 1992, 9, 383–391); thus, entities that modulate pp60$^{c\text{-}src}$-regulated signal transduction pathways offer potential value as antiproliferative agents (Luttrell, D. K.; et al., Involvement of pp60$^{c\text{-}src}$ with Two Major Signaling Pathways in Human Breast Cancer, *Proc. Natl. Acad. Sci. USA.,* 91, 83–87) (Cartwright, C. A., et al., pp60$^{c\text{-}crc}$ Activation in Human Colon Carcinoma,*J. Clin. Invest.* 1989, 83, 2025–2033) (Cartwright, C. A., et al., Activation of the pp60$^{c\text{-}src}$ Protein Kinase is an Early Event in Colonic Carcinogenesis, *Proc. Natl. Acad. Sci. USA.,* 87, 558–562) (Talamonti, M. S., Increase in Activity and Level of pp60$^{c\text{-}src}$ in Progressive Stages of Human Colorectal Cancer, *J. Clin. Invest.* 1993, 91, 53–60) (Ottenhoff-Kalff, et al., Characterization of Protein Tyrosine Kinases from Human Breast: Involvement of the c-src Oncogene Product, *Cancer Res.* 52, 4773–4778).

The src SH2 domain has been the subject of numerous investigations. This domain is a region of approximately 100 amino acids that shares sequence similarity with other members of the src family of proteins, as well as other nonreceptor kinases (abl, lck, fyn, etc.) (Pawson, T.; Gish, G. D.; SH2 and SH3 Domains: From Structure to Function; *Cell* 1992, 71, 359–362), and preferentially binds tyrosine-phosphorylated (Y*) proteins. The SH2 domain may participate in the transmission of signals through the formation of complexes with specific phosphoproteins such as epidermal growth factor receptor (EGFR) (Gilmer, T., et al., Peptide Inhibitors of src SH3-SH2-Phosphoprotein Interactions, *J. Biol. Chem.* 1994, 269, 31711–31719), platelet-derived growth factor receptor (PDGFR) (Mori, S., et al., Identification of Two Juxtamembrane Autophosphorylation Sites in PDGF β-Receptor; Involvement in the src Family Tyrosine Kinases, *EMBO J.* 1993, 12, 2257–2264), and focal adhesion kinase (FAK) (Cobb, B. S., et al., Stable Association of pp60$^{src}$ and pp59$^{fyn}$ with the Focal Adhesion-Associated Protein Tyrosine Kinase, pp125$^{fak}$, *Mol. Cell. Biol.* 1994, 14, 147–155). Alternatively, SH2 domains may act as adapters between phosphorylated receptors and other signaling proteins (Schlessinger, J., SH2/SH3 Signaling Proteins, *Curr. Opin. Genet. Dev.* 1994, 4, 25–30) (Pelicci, G., et al., *Cell* 1992, 70, 93–104) or by regulating the activity of the kinase domain (Cooper, J. A.; Howell, B., The When and How of Src Regulation, *Cell,* 1993, 73, 1051–1054). Thus, an entity that specifically disrupts or inhibits protein-protein interactions involving the src SH2 domain might interrupt signal transduction processes perhaps making such inhibitors useful chemotherapeutic agents.

The term "SH2 domain" is art-recognized, and, as used herein, refers to a protein domain involved in protein-protein interactions, such as a domain of a Src tyrosine kinase that negatively regulates kinase activity. Several SH2 domains have been reported and are typically associated with a regulatory function, e.g., lck, PLCγ1, ZAP. The invention contemplates modulation of activity, such as activity dependent upon protein-protein interactions, mediated by SH2 domains of proteins (e.g., tyrosine kinases such as src, or proteins involved with transmission of a tyrosine kinase signal, such as Grb2) from organisms including mammals, including humans. For examples of SH2 domains, e.g., Smithgall, T. E. *J. Pharmacol. Toxicol. Methods* 1995 34:125–132.

The term "SH3 domain" is art-recognized, and, as used herein, refers to a protein domain involved in protein-protein interactions, such as a domain of a Src tyrosine kinase that negatively regulates kinase activity. Several SH3 domains have been reported and are typically associated with a regulatory function, e.g., GAP, Csk, LcK, Abl. The invention contemplates modulation of activity, such as activity dependent upon protein-protein interactions, mediated by SH3 domains of proteins (e.g., tyrosine kinases such as src, or proteins involved with transmission of a tyrosine kinase signal, such as Grb2) from organisms including mammals, including humans. For examples of SH3 domains, e.g., Smithgall, T. E. *J. Pharmacol. Toxicol. Methods* 1995 34:125–132.

The language "modulating an activity mediated by a SH2 domain, a SH3 domain or tyrosine phosphatase" as used herein, refers to inhibiting, abolishing or increasing the activity of a cell-signaling pathway mediated by a protein including a SH2 domain, a SH3 domain or tyrosine phosphatase e.g., by disrupting protein-protein interactions mediated by SH2 domains. In a preferred embodiment, an activity mediated by an SH2 domain is inhibited, for example, an interaction of GRB2 and SOS is inhibited.

The methods of the invention provide means for inhibiting protein-protein interactions mediated by SH2 domains. Proteins with SH2 domains couple protein-tyrosine kinases to signaling networks involved in growth regulation (see, e.g., Smithgall, op cit. and references cited therein). Disruption of growth-regulatory signal transduction can result in inhibition of cell growth. Accordingly, the invention provides methods for inhibiting growth of cells, including microbial cells and transformed cells, e.g., by inhibiting protein-protein interactions mediated by SH2 domains involved in growth-regulatory signal transduction. Thus, the invention provides methods for treating conditions, e.g., disease states, associated with abnormal or undesired cell growth, including, e.g., fungal or bacterial infections, neoplastic conditions (including cancer), and the like.

To a large degree signal transduction pathways are choreographed by modular SH2 and SH3 domains which mediate highly specific protein:protein interactions. SH2 (Src homology 2) domains are modules of ~100 amino acids that specifically bind phosphotyrosine-containing proteins and peptides (Pawson, T. *Nature* 373:573 (1995); Cohen, G. B. et al. *Cell* 80:237 (1995)). SH3 (Src homology 3) domains are modules of ~60 amino acids that bind to proline-rich sequences (Musacchio, A. et al. *Prog. Biophys. Mol. Biol.* 6:283 (1994); Morton, C. J. et al. *Curr. Biol* 4:615 (1994)). A list of selected therapeutic targets possessing SH2 or SH3 domains is given in Table 4. The design of specific antagonists to these domains holds the promise of targeted treatment of a broad range of pathologies.

TABLE 4

Selected list of SH2- and SH3-containing therapeutic targets and their associated pathologies.

| PATHOLOGY | TARGET | DOMAIN STRUCTURE |
|---|---|---|
| AIDS | Lyn | SH3-SH2-kinase |
|  | Hck | SH3-SH2-kinase |

TABLE 4-continued

Selected list of SH2- and SH3-containing therapeutic targets and their associated pathologies.

| PATHOLOGY | TARGET | DOMAIN STRUCTURE |
|---|---|---|
| Allergy and Asthma | Syk | SH2-SH2-kinase |
|  | Lyn | SH3-SH2-kinase |
| Anemia | SH-PTP1 | SH2-SH2-kinase phosphatase |
| Autoimmune Disease | ZAP | SH2-SH2-kinase |
| Breast Cancer | Grb2 | SH3-SH2-SH3 |
|  | Grb7 | PH-SH2 |
|  | Src | SH3-SH2-kinase |
| Cancer | p85 | SH3-SH2-SH2 |
|  | Shc | SH2 |
|  | Grb2 | SH3-SH2-SH3 |
|  | Gap | SH2-SH3-SH2-PH-GAP |
| CML and ALL | Grb2 | SH3-SH2-SH3 |
|  | CrkL | SH2-SH3-SH3 |
| Erythroleukemias | Shc | SH2 |
| Inflammatory Disease | STATs | DNA-binding-SH3-SH2 |
|  | p47-phox | SH3-SH3 |
|  | p67-phox | SH3-SH3 |
| pre-B-cell-Leukemia | Btk | PH-SH3-SH2-kinase |
| Myelodysplastic Syndrome | Tec | PH-SH3-SH2-kinase |
| Osteoporosis | Src | SH3-Sh2-kinase |

The role of SH2 and SH3 domains in signal transduction has been extensively reviewed (Pawson, T. Nature 373:573 (1995); Cohen, G. B. et al. Cell 80:237 (1995); Schlessinger, J. Curr. Opin. Genet. Dev. 4:25 (1994); Mayer, B. J. et al. Trends Cell Biol. 3:8 (1993); Panayotou et al. Bioessays 15:171 (1993); Carpenter, G. FASEB J. 6:3283 (1992)). In growth factor, cytokine and antigen signaling, occupancy of a receptor by agonist results in receptor dimerization and the phosphorylation of regulatory tyrosines on the cytoplasmic surface (Heldin, C.-H. Cell 80:213 (1995)). Phosphorylation is catalyzed by kinases that are a part of the receptor (receptor tyrosine kinases) or recruited to the receptor from the cytoplasm (non-receptor tyrosine kinases). The resulting phosphotyrosines permit binding of specific SH2-containing proteins and initiate a cascade of sequential protein interactions. Recruited molecules may themselves be tyrosine kinases and catalyze additional cycles of phosphorylation and SH2 recruitment (Cambier, J. C. et al. Curr. Opin. Genet. Dev. 4:55 (1994); tyrosine phosphatases that terminate SH2-mediated associations (Feng, G. S. et al. Trends Genet. 10:54 (1994); Hunter, T. Cell 80:225 (1995)); kinases or phosphatases that activate or inactive previously bound enzymes (Hunter, T. Cell 80:225 (1995)); enzymes that generate lipid-derived second messengers (Divecha, N. Cell 80:269 (1995)); SH2/SH3 adapter proteins that act as docking stations for additional signaling molecules (Downward, J. FEBS Lett. 338:113 (1994)); or proteins that ultimately translocate to the nucleus and regulate transcription (Ihle, J. N. Proc. Soc. Exp. Biol. Med. 206:268 (1994); Darnell, Jr., J. E. et al. Science 264:1415 (1994); Ihle, J. N. et al. TIBS 19:19 (1994); Hill, C. S. Cell 80:199 (1995)). Thus a single event—extracellular binding of agonist—can be coupled to a broad range of cellular responses through a series of SH2- and SH3-mediated events. These cellular responses include proliferation and differentiation (Moodie, S. A. et al. Trends Genet. 10:44 (1994); Ihle, J. N. et al. TIBS 19:19 (1994); Edwards, D. R. Trends Pharm. Sci. 15:239 (1994); Prendergast, G. C. et al. bioessays 16:187 (1994); Myers, M. G. J. et al. TIBS 19:289 (1994); Blenis, J. Proc. Natl. Acad. Sci. USA 90:5889 (1993)), transcription (Ihle, J. N. Proc. Soc. Exp. Biol. Med 206:268 (1994); Darnell, Jr., J. E. et al. Science 264:1415 (1994); Ihle, J. N. et al. TIBS 19:19 (1994); Hill, C. S. Cell 80:199 (1995)), programmed cell death (Green, D. R. et al. Curr. Op. Immunol. 6:476 (1994); Harrington, E. A. et al. Curr. Op. Genet. Dev. 4 (1994); Collins, M. K. et al. Bioessays 16:133 (1994)), adhesion, cytoskeletal rearrangement and chemotaxis (Clark, E. A. et al. Science 268:233 (1995); Bretscher, A. Curr. Opin. Cell. Biol. 5:653 (1993)), exo- and endocytosis (McPherson, P. S. et al. Proc. Natl. Acad. Sci. USA 91:6486 (1994); Miki, H. et al. J. Biol. Chem. 269:5489 (1994)), and assembly and activation of multi-subunit enzyme complexes (Leto, T. L. et al. Proc. Natl. Acad. Sci. USA 91:10650 (1994); Sumimoto, H. et al. Proc. Natl. Acad. Sci. USA 91:5345 (1994); McPhail, L. C. J. Exp. Med 180:2011 (1994)).

SH2 domains are small independently folded protein modules that bind to phosphotyrosine and permit phosphorylation dependent protein:protein interactions. The high affinity and specificity of the interaction permits a small numbers of molecules to survey and report the information state of the cell with a low risk of initiating false signals through random collision with other signaling molecules.

The three dimensional structure of a variety of ligated and unligated SH2 domains have been determined: src (Waksman, G. et al. Cell 72:779 (1993); Gilmer, T. et al. J. Biol Chem. 269:31711 (1994); Xu, R. X. et al. Biochem. 34:2107(1995)), Lck (Eck, M. J. et al. Nature 368:764 (1994)), PLCγ1 (Pascal, S. M. Cell 77:461 (1994)), Abl (Overduin, M. el al. Cell 70:697 (1992); Overduin, M. et al. Proc. Natl. Acad. Sci. USA 89:11673 (1992)), P13K (Booker, G. W. Nature 358:684 (1992)), SH-PTP2 (Lee, C. H. et al. Structure 2:423 (1994)), and the tandem SH2 domains of ZAP-70 (Hatada, M. et al. Nature in press (1995)). Together they define a common structural fold, i.e., a central anti-parallel β-sheet bounded on either side by an α-helix. The two binding sites—one on either side of the β-sheet—are formed by close apposition of the helices to the sheet. The minimal phosphopeptide ligand is four amino acids (pYXXX) with a preference for a hydrophobic residue in the pY+3 position (Songyang, Z. et al. Cell 72:767 (1993)). Bound phosphopeptide is in an extended conformation that straddles the SH2 domain surface and is largely solvent exposed. The bulk of the interactions with the peptide involve phosphotyrosine and the pY+3 residue. Thus binding of phosphopeptide has been described as a "two pronged plug engaging a two-holed socket" (Yu, H. unpublished (1994)). Only a small contribution is made by the pY+1 residue and little or no contact is made by the pY+2 residues or sites outside of the core motif. These structural predictions agree well with in vitro binding data (Gilmer, T. et al. J. Biol. Chem. 269:31711 (1994); Bibbins, K. B. et al. Mol. Cell. Biol. 13:7278 (1993)). The phosphotyrosine binding cleft is formed by three strands of the β-sheet (βB, βC and βD), the loop between βB and βC (BC loop) and αA2 of the A helix (Waksman, G. et al. Cell 72:779 (1993); Gilmer, T. et al. J. Biol. Chem. 269:31711 (1994); Xu, R. X. Biochem. 34:2107 (1995)). The βB strand is the site of the highly conserved FLVRES sequence (Hidaka, M. et al. Biochem. Biophys. Res. Commun. 180:1490 (1991)). The central arginine of this sequence (Arg-178 in Src) is the only invariant residue and forms two hydrogen bonds with phosphate oxygens of the phosphotyrosine. Mutation of Arg-178 abolishes binding (Bibbins, K. B. et al. Mol. Cell. Biol. 13:7278 (1993)). It is likely that the position of this residue deep within the binding pocket places it beyond the reach of phosphoserine and phosphothreonine and thus explains the absence of demonstrable binding to peptides containing these residues. The hydrophobic pY+3 binding pocket is formed by two strands of the β-sheet (βD and βE) and the loops between βE/βF and αB/βG. The precise formation and side-chain composition of this pocket is more variable than that of the phosphotyrosine pocket and generates differences in both affinity and specificity (Marengere, L. E. et al. *Nature* 369:502 (1994); von Bonin, A. et al. *J. Biol. Chem.* 269:33035 (1994)). This is most notable in PLCγ1 and SH-PTP2 (Syp) where the pocket is reshaped to form an extended groove running across the ligand-binding surface (Pascal, S. M. et al. *Cell* 77:461 (1994); Lee, C. H. et al. *Structure* 2:423 (1994)). Molecular dynamic studies using nuclear magnetic resonance spectroscopy indicates that ligand binding induces little structural rearrangement other than side chain position within the binding clefts. Only the BC loop shifts towards a tighter packing with the phosphopeptide and protein core (Farrow, N. A. et al. *Biochem.* 33:5984 (1994)).

The affinity of single SH2 domains for phosphoproteins and phosphopeptides derived from physiological targets range significantly. Using a variety of techniques, estimates from $10^{-5}$ to $10^{-9}$ M have been reported (Songyang, Z. et al. *Cell* 72:767 (1993); Marengere, L. E. et al. *Nature* 369:502 (1994); Zhu, G. et al. *J. Biol. Chem.* 268:1775 (1993); Payne, G. et al. *Proc. Natl. Acad. Sci. USA* 90:4902 (1993); Ladbury, J. E. et al. *Proc. Natl. Acad. Sci. USA* 92:3199 (1995)). Isothermal titration calorimetry suggests that the average change in standard free energy (ΔG') for the interaction between a single SH2 domain and a monophosphorylated ligand is approximately −8.5 kcal.mol$^{-1}$ (Ladbury, J. E. et al. *Proc. Natl. Acad. Sci. USA* 92:3199 (1995)). Essentially no binding is detected when phosphotyrosine is replaced by tyrosine. Dissociation rates are very rapid ($K_{diss}$>0.1 sec$^{-1}$ yielding $t_{1/2}$<0.2 minutes) for single SH2 domains (Zhu, G. et al. *J. Biol. Chem.* 268:1775 (1993); Panayotou, G. et al. *Mol. Cell. Biol.* 13:3567 (1993); Felder, S. et al. *Mol. Cell. Biol.* 13:1449 (1993)). Tandem domains (SH2—SH2) have higher affinity (<$10^{-9}$M) and slower dissociation rates ($K_{diss}$<1.5×$10^{-4}$ sec$^{-1}$ yielding $t_{1/2}$>100 minutes) for tandem binding sites suggesting that specificity, affinity and signal duration can all be amplified by the multimerization of binding domains. Tandem SH2 domains are found in a variety of proteins including Syk, ZAP-70, PLCγ, the p85 subunit of P13K, SH-PTP1 and SH-PTP2.

In vitro studies suggest that for isolated SH2 domains, the difference between the binding affinities of specific and non-specific phosphopeptides ranges from 10–1000 fold (Gilmer, T. et al. *J. Biol. Chem.* 269:31711 (1994); Marengere, L. E. et al. *Nature* 369:502 (1994); Felder, S. et al. *Mol. Cell. Biol.* 13:1449 (1993); Piccione, E. et al. *Biochem.* 32:3197 (1993); Payne, G. et al. *Chem. Biol.* 1:99 (1994)). Using degenerate phosphopeptide libraries, Cantley and colleagues determined the preferred binding sequences for Src, Fyn, Lck, Fgr, Abl, Grb2, Drk, Csk, Vav, SHC, fps/fes, Crk, Nck, Sem5, SH-PTP1, SH-PTP2, Syk, PLCγ1 and the p85 subunit of P13K (Songyang, Z. et al. *Cell* 72:767 (1993); Songyang, Z. et al. *Mol. Cell. Biol.* 14:2777 (1994)). The SH2 domains from p85 selected pYMXM or pYVXM, the exact sequences that have been identified as the p85-binding sites of the PDGF receptor, colony-stimulating factor 1 receptor and c-kit. All members of the Src family that were examined (Src, Fyn, Lyn, Lck and Fgr) selected pYEEI and defined a general consensus of pYEEΨ, where Ψ represents hydrophobic residues. Other members exhibited varying degrees of preference usually with stronger selection for residues at the pY+3 and less selection at pY+1 and Y+2, in concurrence with prediction from structure. An exception to this rule were the SH2 domains from Sem5/Grb2/Drk which exhibited a marked preference for Asn at the pY+2 position and less preference at the pY+1 and pY+3 pockets. It is anticipated that expanding the set of structural monomers beyond the 20 naturally occurring amino acids will permit the synthesis of exquisitely selective SH2 antagonists.

Peptides bind as left-handed polyproline type II helices (Feng, S., et al., *Science*, 266, 1241, 1994) in one of two orientations. Class I peptides bind with their amino-termini making contact with the polar pocket and carboxy-terminal residues intercalating the hydrophobic pockets. Class II peptides bind in the reverse orientation, i.e. with the carboxy-terminus making contact with the polar pocket and amino-terminal residues intercalating the hydrophobic sites. In both cases the same binding sites are occupied; only the orientation is reversed (Feng, S., et al., *Science*, 266, 1241, 1994). Class I versus Class II orientation can be deduced directly from the peptide sequence (Simon, J. and Schreiber, S. L., *Chem. Biol.*, 2, 53, 1995). Class I ligands have the general form Z̲PΨPPΨP and Class II ligands ΨPPΨPPZ̲ where Ψ is any hydrophobic amino and Z̲ is an SH3-domain-specific residue (commonly arginine). When oriented in the binding platform, Z̲ makes contact with the polar binding pocket and the two Ψ-Pro motifs occupy the two hydrophobic pockets. The proline residues that connect the three submotifs, i.e. Z̲PΨPPΨP (Class I) and ΨPPΨPPZ̲ (Class II), form the third, non-contacting ridge of the proline helix and stabilize helix integrity. Class I versus Class II orientation is dictated by several features: the position of the Z̲ residue relative to the Ψ P motifs; the position of the γ and δ methylenes of proline within the pocket; and the uniquely compact nature of the Ψ-Pro dipeptide. In a Ψ-Pro sequence, the $C_\alpha$–$C_\beta$ bond of Ψ is separated from the N–$C_\delta$ bond of proline by two backbone bonds; in a Pro-Ψ sequence, this separation is three backbone bonds. Thus a Pro-Ψ sequence has a composite hydrophobic surface that is significantly larger than that of an Ψ-Pro sequence and can not be accommodated by the binding site (Feng, S., et al., *Science*, 266, 1241, 1994). Details of these features and their precise role in determining orientation are reviewed elsewhere (Feng, S., et al., *Science*, 266, 1241, 1994) (Simon, J. and Schreiber, S. L., *Chem. Biol.*, 2, 53, 1995) (Lim, W. A., et al., *Nature*, 372, 375, 1994).

Estimates of the affinity of single SH3 domains for intact proteins or peptides derived from physiological targets range from >$10^{-3}$ to $10^{-7}$M (Li, N., et al., *Nature*, 363, 85, 1993) (Feng, S., et al., *Science*, 266, 1241, 1994), (Yu, H., et al., *Cell*, 76, 933, 1994) (Kohda, D., et al., *Curr. Biol.*, 2, 1029, 1994) (Chen, J. K., et al., *J. Am. Chem. Soc.*, 115, 12591, 1993) (Rickles, R. J., et al., *EMBO J.*, 13, 5598, 1994) (Lim, W. A., et al., *Protein Sci.*, 3, 1261, 1994) (Rickles, R. J., et al., *Proc. Natl. Acad. Sci. USA* in press, 1995) and are thus generally weaker than SH2/phosphotyrosine interactions. These modest affinities can be enhanced by multimerization. For example, the affinity of the adapter protein Grb2 (SH3-SH2-SH3) has a $K_D$~25 nM for a substrate that permits simultaneous interaction with both SH3 domains (Li, N., et al., *Nature*, 363, 85, 1993). No inherent difference in Class I versus Class II affinity has been reported.

Human pathologies correlated with dysfunction of SH2 domains are listed in Table I and chronic myelogenous leukemia, X-linked agammaglobulinemia, myelodysplastic syndrome, chromic granulomatous disease, severe combined immunodeficiency and faciogenital dysplasia. The precise molecular contributions of these domains in precipitating disease have been identified in several cases. The following examples are chosen to illustrate both the complexity of the cellular signaling pathways and the diversity of roles fulfilled by SH2 and SH3 domains.

Chronic Myelogenous Leukemia (CML) and Acute Lymphoblastic Leukemia (ALL)

A reciprocal translocation between chromosomes 9 and 22 (the so called "Philadelphia chromosome") has been identified in many cases of CML and ALL (Ph+ CML and Ph+ ALL). This translocation results in the juxtaposition of the bcr gene an the abl proto-oncogene (Shtivelman, E., et al., *Nature*, 315,550, 1985) (Clarkson, B., et al., *Leuk. Lymphome*, 2, 81, 1993) (Serra, A., et all, *Leuk. Lymphoma*, 1, 25, 1993) (Puil, L., et al., *EMBO J.*, 13, 764, 1994) (Zhu, Q., et al., *J. Exp. Med.*, 180, 461, 1994) (Vihinen, L., et al., *Biochem. Biophys. Res. Commun.*, 205, 1270, 1994) (Chan, A. C., et al., *Science*, 264, 1599, 1994) (Voss, S. D., et al., *Blood*, 83, 626, 1994) (Pasteris, N. G., et al., *Cell*, 79, 669, 1994) (Iwata, S., et al., *Leukemia*, 8, 1696, 1994) and results in expression of 185 kDa or 210 kDa chimeric Bcr-Abl proteins correlated with ALL and CML, respectively (Chan, L. C., et al., *Nature*, 325, 635, 1987) (Clark, S. S., et al., *Science*, 235, 85, 1987). In both cases, the first 26 amino acids of the proto-oncogene c-Abl are replaced by the first 426 or 927 (or 902) amino acids of Bcr (Shtivelman, E., et al., *Nature*, 315, 550, 1985) (Chan, L. C., et al., *Nature*, 325, 635, 1987) (Clark, S. S., et al., *Science*, 235, 85, 1987). The resulting chimeras localize to the cytoplasm and contain the SH3, SH2 and tyrosine kinase domains of c-abl. The presence of the Bcr sequence deregulates the kinase, an essential requirement for transformation (Pendergast, A. M., et al., *Cell*, 66, 161, 1991) (Muller, A. J., et al., *Mol. Cell. Biol.*, 11, 1785, 1991). Bcr-Abl forms a physical complex with a variety of signaling molecules including Grb2 (Pendergast, A. M., et al., *Cell*, 75, 175, 1993) (Puil, L., et al., *EMBO. J.*, 13, 764, 1994), SH-PTP2 (Tauchi, T., et al., *J. Biol. Chem.* 269, 15381, 1994), and CrkL (ten Hoeve, J., et al., *Cancer Res.*, 54, 2563, 1994). Grb2 is a 25 kDa adapter protein of the form SH3-SH2-SH3 sequence. The SH2 domain of Grb2 recognizes and binds to the bcr-encoded Y177 tyrosine autophosphorylation site in both the p185 and p210 Bcr-Abl proteins. Grb2 in turn associates with mSOS (a Ras guanine nucleotide exchange protein) through a Grb2-SH3/mSOS-poly-proline interaction and (activates the Ras pathway leading to deregulated mitogenic signals (Pendergast, A. M., et al., *Cell*, 75, 175, 1993) (Puil, L., et al., *EMBO J.*, 13, 764, 1994). Mutation of Y177 to phenylalanine (Y177F) abolishes GRB-2 binding and abrogates Bcr-Abl-induced Ras activation and transformation (Pendergast, A. M., et al., *Cell*, 75, 175, 1993). Conversely, point mutations that severely impair the ability of the SH2 domain to bind phosphotyrosine R552L in p185) or removes the major tyrosine autophosphorylation in the kinase domain (Y813F in p185), also impair transformation by Bcr-Abl without effecting Grb2 binding (Afar, D. E., et al., *Science*, 264, 424, 1994). These results suggest that Grb2 binding is necessary, but not sufficient for transformation. The second factor may be CrkL, a 39 kDa adapter protein of the form SH2-SH3-SH3. In neutrophils from normal patients, CrkL is unphosphorylated. In neutrophils from Ph+ CML patients (Oda, T., et al., *J. Biol. Chem.*, 269, 22925, 1994) (Nichols, G. L., et al., *Blood*, 84, 2912, 1994) or bcr-abl transformed cell lines (ten Hoeve, J., et al, *Cancer Res.*, 54, 2563, 1994), CrkL is highly and constitutively tyrosine phosphorylated. Treatment of normal neutrophils with a variety of cytokines and agonists fails to induce CrkL phosphorylation suggesting that this is not part of a normal signaling pathway (Nichols, G. L., et al., *Blood*, 84, 2912, 1994). Furthermore, CrkL forms a physical complex with Bcr-Abl in transformed cells and is readily tyrosine phosphorylated by the Bcr-Abl and c-Abl kinases in vitro (ten Hoeve, J., et al, *Cancer Res.*, 54, 2563, 1994). Together these results implicate CrkL as a second potential oncogenic mediator of Bcr-Abl.

Chronic Granulomatous Disease (CGD)

CGD is characterized by a failure of neutrophils to generate microbicidal oxidants (e.g. superoxide) and leaves CGD patients highly susceptible to opportunistic infections (McPhail, L. C., *J. Exp. Med.*, 180, 2011, 1994). The enzyme responsible, NADPH oxidase, is composed of four proteins: p22-phox, p47-phox, p67-phox and gp91-phox. Activation of NADPH oxidase is regulated through assembly, i.e. upon stimulation of the phagocyte, p47-phox and p67-phox are translocated from the cytosol to the membrane where they associate with the membrane-bound p22-phox/gp91-phox/heme complex and activate superoxide generation. This process relies on a series of SH3-mediated events that begins with the dissociation of an intramolecular proline-rich binding sequence from the p47-phox SH3-domain that unmasks the SH3 domain (Sumimoto, H., et al., *Proc. Natl. Acad. Sci. USA*, 91, 5345, 1994). Following unmasking, both the SH3 and proline-rich sequences become available to participate in other intermolecular interactions. Unmasked p47-phox then associates with p67-phox through SH3-mediated interactions to form a p47/p67 heterodimer (Sumimoto, H., et al., *Proc. Natl. Acad. Sci. USA*, 91, 5345, 1994) which in turn associates with the membrane-bound components through one or both SH3 domains of p47-phox and proline-rich sequences of p22-phox (Sumimoto, H., et al., *Proc. Natl. Acad. Sci. USA*, 91, 5345, 1994). Mutation of Pro-156 to glutamine in the p22-phox disrupts one proline-rich sequence and abolishes binding (Leto, T. L., et al., *Proc. Natl. Acad. Sci., USA*, 91, 10650, 1994), (Sumimoto, H., et al., *Proc. Natl. Acad. Sci. USA*, 91, 5345, 1994). An identical mutation has been found in a patient with CGD (Dinauer, M. C., et al., *Proc. Natl. Acad. Sci. USA*, 88, 11231, 1991), suggesting that it represents a physiological binding sequence. Synthetic peptides corresponding to proline-rich SH3-binding sites of p22-phox or p47-phox effectively block in vitro oxidase assembly and activation (Leto, T. L., et al., *Proc. Natl. Acad. Sci. USA*, 91, 10650, 1994) (Sumimoto, Y., et al., *Proc. Natl. Acad. Sci. USA*, 91, 5345, 1994) (Finan, P., et al., *J. Biol. Chem.*, 269, 13752, 1994).

In one embodiment, the invention provides a method for modulating intracellular signaling pathways by disrupting particular protein-protein interactions mediated by SH2 domains, SH3 domains or tryrosine phosphatase. For instance, the SH2 inhibitors of the present invention can be used to affect the responsiveness of a cell to a growth factor, cytokine or other receptor ligand, and to inhibit the proliferation of transformed cells or to render transformed cells more sensitive to cytostatic or cytotoxic agents. The SH2 target of the subject inhibitors can range from the interaction between, for example, an activated receptor complex and the initial cytoplasmic proteins involved in triggering a particular set of intracellular signaling pathways, to the last SH2-mediated interaction in a specific pathway, such as the formation of a transcription factor complex or allosteric regulation of an enzymatic activity. Thus, the inhibitors of the present invention can be used to inhibit the interaction between an SH2-binding signal transduction protein such as Grb2, and such SH2-containing proteins as, for example, Src, p85, Fyn, Lyn, Hck, Syk, Grb2, Gap, STAT, p47-phox, p67-phox, Btk, and the like.

In a preferred embodiment, the methods of the invention for inhibition of protein-protein interactions mediated by SH2 domains include the step of contacting an SH2 domain with a compound of Formula I. In preferred embodiments, the compound is selected to preferentially inhibit an SH2 domain of an abnormal cell (such as a cancer cell), or a pathogen cell (e.g., a fungal pathogen). Thus, in preferred embodiments, the methods of the invention comprise contacting an SH2 domain of a target protein with a compound of the invention which is selective for the target protein SH2 domain.

Compounds useful in the methods of the invention can be determined by the skilled artisan in light of the teaching herein using no more than routine experimentation. Assays which measure the ability of a compound to inhibit proliferation, to alter the responsiveness of a cell to a growth factor, and the like, will be apparent to the ordinarily-skilled artisan. For example, the ability of a compound of the invention to inhibit cell growth in culture can be measured by standard assays.

In another aspect, the invention provides libraries of compounds of Formula I. Libraries of the invention are useful, e.g., for drug discovery. For example, a library of the invention can be screened (e.g., according to the methods described herein) to determine whether the library includes compounds having a pre-selected activity. Thus, for example, a library can be screened to determine whether compounds of the library have SH2/SH3 domain binding activity or any other activity, e.g., tyrosine phosphatase, which can be detected in vitro or in vivo, e.g., anti-inflammatory activity, cell growth stimulatory activity, antineoplastic activity, and the like.

The synthesis of combinatorial libraries is well known in the art and has been reviewed (see, e.g., E. M. Gordon et al, *J. Med. Chem.* 37:1385–1401 (1994)). Thus, the subject invention contemplates methods for synthesis of combinatorial libraries of compounds of Formula I. Such libraries can be synthesized according to a variety of methods. For example, a "split-pool" strategy can be implemented in the following way: beads of a functionalized polymeric support (such as Wang resin) are placed in a plurality of reaction vessels. To each aliquot of beads is added a solution of an N-Boc protected amino acid, and a coupling reagent (e.g., DCC) is added to each vessel. The reactions are allowed to proceed to yield a plurality of immobilized amino acids. The aliquots of derivatized beads are then washed, "pooled" (i.e., recombined), the N-Boc protecting group is removed (e.g., with a solution of TFA in DCM) and the pool of beads is again divided, with each aliquot being placed in a separate reaction vessel. To each reaction vessel is added a solution of an aldehyde (e.g., an aldehyde such as compound 6 of Scheme 1) and a reducing agent such as sodium cyanoborohydride, and reductive amination occurs to yield a plurality of reaction vessels each containing a plurality of compounds immobilized on solid support. The library of immobilized compounds can then be washed to remove impurities. In certain embodiments, the library of compounds can be further treated, e.g, by deprotection and derivatization of the amino functionality. Further processing can optionally include cleavage from the solid support, if desired, and further reaction (e.g, substitution or further functionalization).

In another illustrative method of combinatorial synthesis, a "diversomer library" is created by a modification of the method of Hobbs DeWitt et al. (*Proc. Natl. Acad. Sci. USA.* 90:6909 (1993)). Other synthesis methods, including the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J. Med. Chem.*, op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assay formats useful for screening the libraries of the invention are known in the art (see, e.g., E. M. Gordon et al., *J. Med. Chem.* 37:1385–1401 (1994)).

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 2 compounds, more preferably at least about 30 compounds, more preferably at least about 100 compounds, more preferably at least about 500 compounds, and still more preferably at least about 1000 compounds. In certain embodiments, the libraries of the invention can include at lest $10^4$ compounds, $10^5$ compounds, $10^6$ compounds, or $10^7$ compounds. However, in certain preferred embodiments, the libraries of compounds of the invention contain fewer than $10^9$ compounds, more preferably fewer than $10^8$ compounds, and still more preferably fewer than $10^7$ compounds.

A library of compounds is preferably substantially pure, i.e., substantially free of compounds other than the intended products, e.g, members of the library. In preferred embodiments, the purity of a library produced according to the methods of the invention is at least about 50%, more, preferably at least about 70%, still more preferably at least about 90%, and most preferably at least about 95%.

The libraries of the invention can be prepared according to the methods described herein, or by other synthetic methods which will be apparent to the ordinarily-skilled artisan. In general, such methods will involve the preparation of libraries by providing variegated populations of compositions of Formula I. The term "variegated population", as used herein, refers to a population including at least two different chemical entities, erg., of different chemical structure. For example, a "variegated population" of amino acids would comprise at least two different amino acids. Similarly, a variegated population of spirolactams comprises at least two different spirolactams.

In another aspect, the invention provides pharmaceutical compositions comprising a compound of the invention, Formula I, or a pharmaceutically-acceptable salt thereof, and a pharmaceutically-acceptable carrier.

The pharmaceutical compositions of the invention comprise a therapeutically-effective amount of one or more of the compounds described above (e.g., Compounds of Formula I), formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect, e.g., treating (i.e., preventing or ameliorating) cancer in a subject, or inhibiting protein-protein interactions mediated by an SH2 domain in a subject, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds can contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 per cent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound of the invention in the proper medium. Absorption enhancers can also be used to increase the flux of the compound of the invention across the skin. The rate of such flux can be controlled by either providing a rate controlling membrane or dispersing the compound of the invention in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral or topical administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the derivative (e.g., ester, salt or amide) thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient, when used for the indicated effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The invention is further illustrated by the examples in Appendices A through D which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

EXAMPLES

The invention is further illustrated by the following examples, which should not be construed as limiting. Numbered compounds in the following examples refer to the correspondingly numbered compounds shown in Scheme 5 above.

Example 1

Synthesis of 1-Diisopropyloxyphosphorylmethyl-4-Benzyloxy-2-Pyridone

A mixture of 4-benzyloxy-2(1H)-pyridone (1.01 g, 5.00 mmol), diisopropyl bromomethylphosphonate (1.94 g, 7.50 mmol) and potassium carbonate (2.76 g, 20.0 mmol) in acetonitrile (25.0 mL) was refluxed for 6 hr. Diisopropyl bromomethylphosphonate (1.94 g, 7.50 mmol) was then added to the mixture and continued to reflux for 14 hr. After cooling down to room temperature, the mixture was filtered and the filtrate was concentrated in vacuo. Water was added to the residue and the aqueous mixture was extracted with ethyl acetate (3×). The combined ethyl acetate solution was dried ($Na_2SO_4$), filtered and the filtrate was concentrated in vacuo to dryness. The residue was subjected to column chromatography (ethyl acetate:methanol=10:1) to give 1.97 g (98%) of 1-diisopropyloxyphosphorylmethyl-4-benzyloxy-2-pyridone as the colorless oil. $^1$H NMR (200 MHz, $CDCl_3$) δ1.22 (s, 3H), 1.25 (s, 3H), 1.26 (s, 3H), 1.29 (s, 3H), 4.34–4.09 (d, J=12.6 Hz, 2H), 4.60–4.76 (m, 2H), 4.94 (s, 2H), 5.93–5.98 (m, 2H), 7.31–7.41 (m, 6H); $^{13}$C NMR (50.3 MHz, $CDCl_3$) δ23.6, 23.7, 23.8, 23.9, 40.3, 43.4, 71.0, 71.9, 97.8, 101.3, 127.6, 128.4, 128.6, 135.2, 137.5, 163.1, 167.0, 171.1; IR (film) ν982, 1177, 1228, 1351, 1598, 1654, 2933, 2979 $cm^-$; MS (ES): 380.0 ($M^++1$).

The following compounds were obtained in a manner similar to that of Example 1:

1-(tert-butyloxycarbonylmethyl)-4-benzyloxy-2-pyridone. $^1$H NMR (200 MHz, $CDCl_3$) δ1.47 (s, 9H), 4.48 (s, 2H), 4.97 (s, 2H), 5.94–6.03 (m, 2H), 7.05–7.09 (d, J=8.0 Hz, 1H), 7.35–7.39 (m, 5H).

1-(3-methoxycarbonylpropyl-1)-4-benzyloxy-2-pyridone. $^1$H NMR (200 MHz, $CDCl_3$) δ2.00–2.07 (m, 2H), 2.33–2.40 (t, J=7.0 Hz, 2H), 3.67 (s, 3H), 3.88–3.95 (t, J=7.0 Hz, 2H), 4.97 (s, 2H), 5.93–5.97(m, 2H), 7.12–7.16 (d, J=8.0 Hz, 1H), 7.33–7.40 (m, 5H).

Example 2

Synthesis of 1-Diisopropyloxyphosphorylmethyl-4-Hydroxy-2-Pyridone

A solution of 1-diisopropyloxyphosphorylmethyl-4-benzyloxy-2-pyridone (1.21 g, 3.20 mmol) in methanol (10.0 mL) was bubbled with hydrogen for 2 min. Palladium charcoal (0.60 g) was added. The mixture was stirred at room temperature for 2 hr under a filled hydrogen balloon and filtered. The filtrate was concentrated in vacuo to dryness to give 0.89 g (96%) of 1-diisopropyloxyphosphorylmethyl-4-hydroxy-2-pyridone as colorless solid. Mp 143–144° C. (dichloromethane/hexanes); $^1$H NMR (200 MHz, $CDCl_3$) δ1.26 (s, 3H), 1.29 (s, 3H), 1.33 (s, 3H), 1.36 (s, 3H), 4.32–4.39 (d, J=12.4 Hz, 2H), 4.63–4.80 (m, 2H), 5.95–5.98 (m, 1H), 6.01–6.06 (dd, J=2.4, 7.3 Hz, 1H), 7.33–7.37 (d, J=7.3 Hz, 1H); $^{13}$C NMR (50.3 MHz, $CDCl_3$) δ23.6, 23.7, 23.8, 23.9, 40.8, 44.0, 72.3, 72.4, 99.3, 102.8, 137.9, 164.1, 168.3; MS (FAB): 290 ($M^++1$), 248, 206, 188; HRMS: calcd for $C_{12}H_{20}NO_5P+H$: 290.1158, found: 290.1146.

The following compounds were obtained in a manner similar to that of Example 2:

1-(tert-butyloxycarbonylmethyl)-4-hydroxy-2-pyridone. $^1$H NMR (200 MHz, $CDCl_3$) δ1.29 (s, 9H), 4.31 (s, 2H), 5.72–5.73 (d, J=2.6 Hz, 1H), 5.78–5.83 (dd, J=2.6, 7.6 Hz, 1H), 6.93–6.97(d, J=7.6 Hz, 1H).

1-(3-methoxycarbonylpropyl-1)-4-hydroxy-2-pyridone. $^1$H NMR (200 MHz, $CDCl_3$) δ1.71–1.85 (m, 2H), 2.08–2.15 (t, J=7.0 Hz, 2H), 3.42 (s, 3H), 3.63–3.70 (t, J=7.0 Hz, 2H), 5.63–5.64 (dd, J=2.4 Hz, 1H), 5.68–5.73 (dd, J=2.4, 7.2 Hz, 1H), 6.92–6.95 (d, J=7.2 Hz, 1H).

Example 3

Synthesis of 1-Diisopropyloxyphosphorylmethyl-4-Trifluoromethanesulfonyloxy-2-Pyridone To a solution of 1-diisopropyloxyphosphorylmethyl-4-hydroxy-2-pyridone (0.44 g, 1.52 mmol) in dichloromethane (18.0 mL) was added triethylamine (0.17 g, 0.23 mL, 1.67 mmol) at −78° C. followed by the addition of trifluoromethanesulfonic anhydride (0.47 g, 0.28 mL, 1.67 mmol). The resulted mixture was stirred at 78° C. for 5 min and quenched with ammonium chloride solution. After warming to room temperature, water and dichloromethane was added and separated. The aqueous solution was extracted with dichloromethane and the dichloromethane solution was dried ($Na_2SO_4$) and filtered. The filtrate was concentrated in vacuo to dryness and the residue was passed through a thin layer of silica gel to give 0.43 g (67%) of 1-diisopropyloxyphosphorylmethyl-4-trifluoromethanesulfonyloxy-2-pyridone as a colorless solid. $^1$H NMR (200 MHz, $CDCl_3$) δ1.25 (s, 3H), 1.28 (s, 3H), 1.30 (s, 3H), 1.33 (s, 3H), 4.35–4.42 (d, J=14 Hz, 2H), 4.65–4.79 (m, 2H), 6.18–6.24 (dd, J=2.8, 7.7 Hz, 1H), 6.49–6.50 (d, J=2.8 Hz, 1H), 7.64–7.68 (d, J=7.7 Hz, 1H); MS (FAB): 422 ($M^++1$), 380, 338, 320; HRMS: calcd for $C_{13}H_{19}F_3NO_7PS+H$: 422.065 1, found: 422.0579.

The following compounds were obtained in a manner similar to that of Example 3:

1-(tert-butyloxycarbonylmethyl)-4-trifluoromethanesulfonyloxy-2-pyridone. $^1$H NMR (200 MHz, $CDCl_3$) δ1.48 (s, 9H), 4.55 (s, 2H), 6.19–6.24 (dd, J=2.6, 7.6 Hz, 1H), 6.49–6.51 (d, J=2.6 Hz, 1H), 7.31–7.35 (d, J=7.6 Hz, 1H). MS (ES): 358.1 ($M^++1$), 343.0, 302.0.

1-(3-methoxycarbonylpropyl-1-4-trifluoromethanesulfonyloxy-2-pyridone. $^1$H NMR (200 MHz, $CDCl_3$) δ1.99–2.13 (m, 2H), 2.35–2.42 (t, J=6.8 Hz, 2H), 3.68 (s, 3H), 3.96–4.03 (t, J=7.4 Hz, 2H), 6.16–6.21 (dd, J=2.8, 7.6 Hz, 1H), 6.46–6.48 (d, J=2.8 Hz, 1H), 7.41–7.44 (d, J=7.6 Hz, 1H).

Example 4

Synthesis of N-(tert-Butoxycarbonyl)-3-(1-Diisopropyloxyphosphorylmethyl-2-Pyridone-4-yl)-1-Alanine Benzyl Ester To a suspension of zinc (1.177 g, 18.0 mmol) in tetrahydrofuran (2.40 mL) was added dibromoethane (0.169 g, 0.078 mL, 0.90 mmol). The mixture was heated with hot air gun to reflux and then cooled down. The heating was repeated five times. The reaction vessel was then immersed in an 35° C. oil bath followed by the addition of chlorotrimethylsilane (0.02 g, 0.023 mL, 0.18 mmol). The mixture was stirred at 35° C. for 0.5 hr. To this resulted mixture was added the solution of N-(tert-butoxycarbonyl)-3-iodo-D-alanine benzyl ester (2.43 g, 6.00 mmol) in tetrahydrofuran-dimethylacetamide (1:1, 12.0 mL) and continued stirring for 0.5 hr at 35° C. The solution of 1-diisopropyphosphorylmethyl-4-trifuoromethanesulfonyloxy-2-pyridone (1.26 g, 3.00 mmol) in tetrahydrofuran-dimethylacetamide (1:1, 12.0 mL) was then added followed by the addition of tris(dibenzylideneacetone)dipalladium(0) (0.28 g, 0.30 mmol) and tri-o-tolylphosphine (0.18 g, 0.60 mmol). The resulted mixture was then stirred at 55° C. for 3 hr. After cooling down to room temperature, ethyl acetate was added. The mixture was filtered, the filtrate was poured onto 0.10 N hydrochloride solution and separated. The aqueous solution was extracted with ethyl acetate and the combined ethyl acetate solution was dried ($Na_2SO_4$) and filtered. The filtrate was concentrated in vacuo to dryness and t he residue was subjected to column chromatography (ethyl acetate) to give 0.0.73 g (43%) of N-(tert-butoxycarbonyl)-3-(1-diisopropyloxyphosphorylmethyl-2-pyridone-4-yl)-1-alanine benzyl ester. $^1$H NMR (200 MHz, $CDCl_3$) δ1.23 (s, 3H), 1.26 (s, 3H), 1.28 (s, 3H), 1.31 (s, 3H), 1.41 (s, 9H), 2.74–3.01 (m, 2H), 4.30–4.38 (dd, J=3.6, 12.8 Hz, 2H), 4.54–4.74 (m, 3H), 5.01–5.05 (d, J=7.8 Hz, 1H), 5.15 (s, 2H), 5.86–5.89 (d, J=6.6 Hz, 1H), 6.32 (s, 1H), 7.26–7.37 (m, 6H); ); $^{13}$C NMR (50.3 MHz, $CDCl_3$) δ23.7, 23.8, 23.9, 24.0, 28.2, 37.6, 40.9, 44.1, 53.1, 67.5, 72.0, 72.2, 77.3, 80.4, 107.6, 120.3, 128.7, 135.0, 137.3, 149.5, 155.1, 161.6, 171.1; IR (film) v986, 1165, 1243, 1365, 1597, 1665, 1711, 1745, 2931, 2977 $cm^{-1}$; MS (ES): 551 ($M^+$1), 495.

Example 5

Synthesis of N-(tert-Butoxycarbonyl)-3-(1-Diisopropyloxyphosphorylmethyl-2-Pyridone-4-yl)-1-Alanine After bubbling the solution of N-(tert-butoxycarbonyl)-3-(1-diisopropyloxyphosphorylmethyl-2-pyridone-4-yl)-1-alanine benzyl ester (0.32 g, 0.59 mmol) in methanol (10.0 mL) with hydrogen for 3 min, palladium on charcoal (0.16 g) was added. The mixture was then stirred under a filled hydrogen balloon for 14 hr and filtered. The filtrate was concentrated in vacuo to dryness to give 0.27 g (99%) of N-(tert-butoxycarbonyl)-3-(1-diisopropyloxyphosphorylmethyl-2-pyridone-4-yl)-1-alanine. $^1$H NMR (200 MHz, $CDCl_3$) δ1.21 (s, 3H), 1.24 (s, 3H), 1.28 (s, 3H), 1.31 (s, 3H), 1.43 (s, 9H), 2.94–3.02 (m, 2H), 4.28–4.75 (m, 5H), 5.40 (br, 1H), 6.26–6.29 (d, J=6.6 Hz, 1H), 6.56 (s, 1H), 7.43–7.46 (d, J=6.6 Hz, 1H).

Example 6

To a solution of N-(tert-butoxycarbonyl)-3-(1-diisopropyloxyphosphorylmethyl-2-pyridone-4-yl)-1-alanine (0.241 g, 0.523 mmol) and $NH_2$-Val-Ala-$CONBu_2$ (0.189 g, 0.630 mmol) in N,N-dimethylformamide (5.00 mL) was added 1-hydroxybenzotriazole (0.071 g, 0.523 mmol) and 4-dimethylaminopyridine (0.01 mmol). The mixture was then cooled down to 0° C. and 1-(3-dimethylaminopropyl)-3-ethylcarbodiimide hydrochloride (0.201 g, 1.05 mmol) was added. The resulted mixture was stirred at room temperature for 14 hr. Water was added and the mixture was extracted with ethyl acetate (3×). The combined ethyl acetate solution was dried ($Na_2SO_4$), filtered. The filtrate was concentrated in vacuo to dryness. The residue was subjected to column chromatography (ethyl acetate) to give 0.33 g (85%) of the desired product 13 (See Scheme 5 above). $^1$H NMR (200 MHz, $CDCl_3$) δ0.84–0.95 (m, 2H), 1.17–1.55 (m, 32H), 2.01–2.13 (m, 1H), 2.74–3.29 (m, 4H), 3.37–3.52 (m, 2H), 4.28–4.41 (m, 4H), 4.57–4.85 (m, 3H), 5.46–5.50 (d, J=8.0 Hz, 1H), 6.13–6.17 (d, J=7.0 Hz, 1H), (s, 1H), 6.92–6.96 (d, J=8.0 Hz, 1H), 7.19–7.23 (d, J=8.0 Hz, 1H), 7.58–7.42 (d, J=7.0 Hz, 1H); MS (ES): 742 ($M^+$+1).

The following compound was obtained in a manner similar to that of Example 6:

Compound 11: NMR (200 MHz, $CDCl_3$) δ0.84–0.97 (m, 12H), 1.21–1.65 (m, 23H), 1.95 (s, 3H), 2.20–2.40 (br, 1H), 2.75–2.95 (m, 2H), 3.11–3.45 (m, 4H), 4.31–4.40 (dd, J=5.2, 13.0 Hz, 2H), 4.49–4.97 (m, 5H), 6.11–6.14 (d, J=6.8 Hz, 1H), 6.35 (s, 1H), 6.89–6.93 (d, J=8.8 Hz, 1H), 7.40–7.50 (m, 2H), 7.75–7.80 (d, J=8.4 Hz, 1H); $^{13}$C NMR (50.3 MHz, $CDCl_3$) δ13.8, 18.2, 18.9, 19.4, 19.9, 20.1, 22.7. 23.7, 23.8, 23.9, 24.0, 29.6, 31.4, 31.6, 37.9, 40.9, 44.0, 44.7, 45.8, 47.5, 52.6, 58.2, 71.9, 72.0, 107.5, 120.2, 137.3, 150.2, 161.6, 170.1, 170.6, 170.8, 172.1; IR (film) v987, 1105, 1241, 1375, 1464, 1540, 1623, 1680, 1690 $cm^{-1}$.

Example 7

To a solution of 13 (0.092 g, 0.125 mmol) in dichloromethane (1.50 mL) was added bis(trimethylsilyl)trifluoroacetamide (0.0.48 g, 0.50 mL, 1.87 mmol). After being stirred at room temperature for 1 hr, the mixture was cooled down to 0° C. followed by the addition of iodotrimethylsilane (0.35 g, 0.25 mL, 1.74 mmol). The resulted mixture was stirred at 0° C. for 1 hr and at room temperature for 2 hr and then concentrated in vacuo to dryness. The residue was treated with a mixture of trifluoroacetic acid-:water:acetonitrile (3:5:10) for 1.5 hr at room temperature. After the solvent was removed in vacuo, 0.069 g (100%) of the desired product was obtained. $^1$H NMR (200 MHz, $CD_3OD$) δ0.80–1.05 (m, 12H), 1.31–1.74 (m, 10H), 1.97–2.20 (m, 2H), 3.30–3.50 (m, 3H), 4.18–4.45 (m, 4H), 4.70–4.95 (m, 2H), 6.36–6.40 (d, J=7.0 Hz, 1H), 6.45 (s, 1H), 7.70–7.74 (d, J=7.0 Hz, 1H), 8.20–8.25 (d, J=8.2 Hz, 1H); MS (ES): 558.3 ($M^+$+1).

Example 8

Synthesis of N-Acetyl-3-(1-Diisopropyloxyphosphorylmethyl-2-Pyridone-4-yl)-1-Alanine Benzyl Ester After treatment of N-(tert-butoxycarbonyl)-3-(1-diisopropyloxyphosphorylmethyl-2-pyridone-4-yl)-1-alanine benzyl ester (0.14 g, 0.26 mmol) with 25% of trifluoroacetic acid in dichloromethane (2.90 mL) for 15 min at room temperature, the mixture was concentrated in vacuo to dryness to give 3-(1-diisopropyloxyphosphorylmethyl-2-pyridone-4-yl)-1-alanine benzyl ester. The obtained material was dissolved in dichloromethane (5.00 mL) and cooled down to 0° C. To this solution was added N-methylmorpholine (0.078 g, 0.77 mmol) and acetic anhydride (0.04 g, 0.037 mL, 0.39 mmol). The resultant mixture was stirred at room temperature for 14 hr. Water was added and separated, the aqueous layer was extracted with dichloromethane (2×). The combined dichloromethane solution was dried ($Na_2SO_4$) and filtered. The filtrate was concentrated in vacuo to dryness and the residue was subjected to column chromatography (ethyl acetate) to 0.096 g (76%) of N-acetyl-3-(1-diisopropyloxyphosphorylmethyl-2-pyridone-4-yl)-1-alanine benzyl ester. $^1$H NMR (200 MHz, CDCl$_3$) δ1.22 (s, 3H), 1.25 (s, 3H), 1.27 (s, 3H), 1.30 (s, 3H), 1.97 (s, 3H), 2.76–2.87 (dd, J=6.4, 14 Hz, 1H), 2.92–3.01 (dd, J=6.4, 14 Hz), 4.27–4.37 (dd, J=7.6, 13.2 Hz, 2H), 4.60–4.76 (m, 2H), 4.82–4.92 (dd, J=6.4, 6.4 Hz, 1H), 5.14 (s, 2H), 5.84–5.88 (dd, J=1.8, 7.6 Hz, 1H), 6.21–6.27 (m, 2H), 7.29–7.36 (m, 6H); $^{13}$C NMR (50.3 MHz, CDCl$_3$) δ23.7, 23.8, 23.9, 24.0, 37.2, 41.0, 44.1, 51.8, 67.6, 72.0, 72.1, 107.6, 120.2, 128.7, 128.8, 134.9, 137.3, 149.4, 161.5, 169.9, 171.0; IR (film) v990, 1239, 1595, 1665, 1708, 1743, 2931, 2977 cm$^{-1}$.

Example 9

N-Acetyl-3-(1-Diisopropyloxyphosphorylmethyl-2-Pyridone-4-yl)-1-Alanine

After bubbling the solution of N-acetyl-3-(1-diisopropyloxyphosphorylmethyl-2-pyridone-4-yl)-1-alanine benzyl ester (0.12 g, 0.25 mmol) in methanol (10.0 mL) with hydrogen for 3 min, palladium hydroxide (0.06 g) was added. The mixture was then stirred under a filled hydrogen balloon for 3 hr and filtered. The filtrate was concentrated in vacuo to dryness to give 0.093 g (94%) of N-acetyl-3-(1-diisopropyloxyphosphorylmethyl-2-pyridone-4-yl)-1-alanine. Mp. 96–98° C.; 1H NMR (200 MHz, CDCl$_3$) δ1.28 (s, 3H), 1.30 (s, 3H), 1.33 (s, 3H), 1.35 (s, 3H), 1.96 (s, 3H), 2.95–3.20 (m, 2H), 4.27–4.55 (m, 4H), 4.64–4.79 (m, 1H), 4.90 (br, 1H), 6.16–6.19 (d, J=6.0 Hz, 1H), 6.48 (s, 1H), 7.41–7.45 (d, J=6.0 Hz, 1H); $^{13}$C NMR (50.3 MHz, CDCl$_3$) δ23.7, 23.8, 23.9, 24.0, 36.9, 41.9, 45.0, 52.8, 72.5, 72.6, 109.5, 119.6, 137.2, 151.8, 162.4, 171.0, 175.2; IR (film) v992, 1235, 1546, 1628, 1724, 2964 cm$^{-1}$; MS (ES): 403.2 (M$^+$+1).

Example 10

Synthesis of 1-Diisopropyloxyphosphorylmethyl-4-Phenyl-2-Pyridone

A solution of 1-diisopropyloxyphosphorylmethyl-4-trifluoromethanesulfonyloxy-2-pyridone (0.08 g, 0.79 mmol) and tetrakis(triphenylphosphine)palladium(0) (0.011 g, 0.0095 mmol) in dimethoxyethane (1.00 mL) was stirred at room temperature for 15 min followed by the addition of the solution of phenylboronic acid (0.026 g, 0.21 mmol) in dimethoxyethnae (1.00 mL) and 2M sodium carbonate (1.00 mL). The resulted mixture was refluxed for 14 hr and cooled down to room temperature. Water and ethyl acetate were added. After separation, the aqueous layer was extracted with ethyl acetate (2×). The combined ethyl acetate solution was dried (Na$_2$SO$_4$) and filtered, the filtrate was concentrated in vacuo to dryness. The residue was subjected to preparative thin layer chromatography (ethyl acetate) to give 0.039 g (64%) of 1-diisopropyloxyphosphorylmethyl-4-phenyl-2-pyridone. $^1$H NMR (200 MHz, CDCl$_3$) δ1.26 (s, 3H), 1.29 (s, 3H), 1.30 (s, 3H), 1.33 (s, 3H), 4.40–4.47 (d, J=13.2 Hz, 2H), 4.65–4.82 (m, 2H), 6.45–6.50 (dd, J=1.8, 7.4 Hz, 1H), 6.81–6.82 (d, J=1.8 Hz, 1H), 7.43–7.49 (m, 3H); 7.54–7.62 (m, 3H).

The following compounds were obtained in a manner similar to that of Example 10:

1-diisopropyloxyphosphorylmethyl-4-(2-methylphenyl)-2-pyridone. $^1$H NMR (200 MHz, CDCl$_3$) δ1.26 (s, 3H), 1.29 (s, 3H), 1.30 (s, 3H), 1.33 (s, 3H), 2.27 (s, 3H), 4.41–4.48 (d, J=13.0 Hz, 2H), 4.65–4.82 (m, 2H), 6.16–6.20 (dd, J=2.0, 7.0 Hz, 1H), 6.50–6.51 (d, J=2.0 Hz, 1H), 7.17–7.27 (m, 4H); 7.51–7.54 (d, J=7.0 Hz, 1H); $^{13}$C NMR (50.3 MHz, CDCl$_3$) δ20.1, 23.6, 23.7, 23.9, 24.0, 41.1, 44.2, 72.0, 72.1, 108.5, 119.6, 126.1, 128.5, 128.6, 130.7, 134.8, 136.8, 138.4, 153.8, 161.8.

1-diisopropyloxyphosphorylmethyl-4-(3-nitrophenyl)-2-pyridone. 1H NMR (200 MHz, CDCl$_3$) δ1.27 (s, 3H), 1.29 (s, 3H), 1.30 (s, 3H), 1.33 (s, 3H), 4.41–4.47 (d, J=13.0 Hz, 2H), 4.66–4.82 (m, 2H), 6.44–6.49 (dd, J=1.0, 7.2 Hz, 1H), 6.82 (s, 1H), 7.60–7.68 m, 2H), 7.87–7.92 (m, 1H); 8.24–8.31 (m, 1H), 8.41 (s, 1H).

1-diisopropyloxyphosphorylmethyl-4-(2-thienyl)-2-pyridone. $^1$H NMR (200 MHz, CDCl$_3$) δ1.25 (s, 3H), 1.28 (s, 3H), 1.30 (s, 3H), 1.32 (s, 3H), 4.37–4.43 (d, J=12.8 Hz, 2H), 4.64–4.78 (m, 2H), 6.43–6.47 (m, 1H), 6.79 (s, 1H), 7.07–7.12 (m, 1H), 7.39–7.43 (m, 2H), 7.48–7.52 (d, J=7.2 Hz, 1H); $^{13}$ C NMR (50.3MHz, CDCl$_3$) δ23.7, 23.8, 23.9, 24.0, 41.0, 44.1, 72.1, 72.2, 104.6, 114.3, 126.5, 128.1, 128.5, 137.7, 140.3, 144.7, 161.9; IR (film) v979, 1104, 1240, 1341, 1595, 1655, 2931, 2978 cm$^{-1}$; MS (ES): 356.0 (M$^+$+1), 272.0.

Example 11

Synthesis of 1-Diisopropyloxyphosphorylmethyl-4-(2-Methoxyphenyl)-2-Pyridone

A mixture of 1-diisopropyloxyphosphorylmethyl-4-trifluoromethanesulfonyloxy-2-pyridone (0.169 g, 0.40 mmol), tetrakis(triphenylphosphine)palladium(0) (0.046 g, 0.04 mmol), 2-methoxyphenylboronic acid (0.067 g, 0.44 mmol) and potassium carbonate (0.22 g, 1.60 mmol) in tetrahydrofuran-dimethylacetamide (1:1, 4.00 mL) was shaken on J-KEM shaker for 48 hr and poured onto water. The mixture was separated and the aqueous layer was extracted with ethyl acetate (3×). The ethyl acetate solution was dried (Na2SO4) and filtered. The filtrate was concentrated in vacuo to dryness and the residue was subjected to preparative thin layer chromatography (ethyl acetate) to give 0.12 g (78%) 1-diisopropyloxyphosphorylmethyl-4-(2-methoxyphenyl)-2-pyridone. $^1$H NMR (200 MHz, CDCl$_3$) δ1.26 (s, 3H), 1.28 (s, 3H), 1.29 (s, 3H), 1.32 (s, 3H), 3.79 (s, 3H), 4.39–4.45 (d, J=12.8 Hz, 2H), 4.64–4.79 (m, 2H), 6.41–6.45 (dd, J=1.8, 7.4 Hz, 1H), 6.71–6.72 (d, J=1.8 Hz, 1H), 6.92–7.03 (m, 2H), 7.27–7.39 (m, 2H); 7.45–7.48 (d, J=7.4 Hz, 4H); $^{13}$C NMR (50.3 MHz, CDCl$_3$) δ23.6, 23.7, 23.9, 24.0, 41.0, 44.1, 55.4, 71.9, 72.1, 108.7, 111.4, 119.6, 120.9, 127.0, 129.9, 130.5, 136.0, 150.4, 156.7, 162.1; IR (film) v985, 1178, 1248, 1348, 1576, 1654, 293, 2979 cm$^{-1}$ The following compounds were obtained in a manlner similar to that of Example 11:

1-diisopropyloxyphosphorlmethyl-4(2-trifluoromethylphenyl)-2-pyridone. $^1$H NMR (200 MHz, CDCl$_3$) δ1.25 (s, 3H), 1.28 (s, 3H), 1.29 (s, 3H), 1.32 (s, 3H), 4.41–4.48 (d, J=13.0 Hz, 2H), 4.64–4.80 (m, 2H), 6.16–6.19 (d, J=7.07 Hz, 1H), 6.51 (s, 1H), 7.25 (m, 1H), 7.42–7.73 (m, 4H); $^{13}$C NMR (50.3 MHz, CDCl$_3$) δ23.6, 23.7, 23.9, 24.0, 41.1,44.2, 72.1, 72.2, 108.0, 120.1, 121.1, 126.2, 126.3, 126.4, 126.5, 126.9, 127.5, 128.1, 128.4, 128.7, 128.8, 130.4, 131.5, 131.8, 131.9, 132.0, 132.2, 133.6, 136.7, 137.6, 137.7, 151.7, 161.3; IR (film) v981, 1107, 1125, 1166, 1241, 1313, 1595, 1663,2 29)3, 2981 cm$^{-1}$.

1-diisopropyloxyphosphorylmethyl-4-(3-chlorophenyl)-2-pyridone. $^1$H NMR (200 MHz, CDCl$_3$) δ1.25 (s, 3H), 1.28 (s, 3H), 1.29 (s, 3H), 1.32 (s, 3H), 4.39–4.45 (d, J=13.0 Hz, 2H), 4.64–4.80 (m, 2H), 6.37–6.42 (dd, J=2.0, 7.2 Hz, 1H), 6.73–6.74 (d, J=2.0 Hz, 1H), 7.35–7.42 (m, 3H), 7.52 (s, 1H), 7.55–7.59 (d, J=7.2 Hz, 1H); $^{13}$C NMR (50.3 MHz, CDCl$_3$) δ23.7, 23.8, 23.9, 24.0, 41.1, 44.2, 72.0, 72.2, 105.35, 117.1, 124.9, 126.9, 129.5, 130.3, 135.0, 137.9, 139.2, 150.4, 161.8; IR (film) ν981, 1102, 1199, 1239, 11346, 1592, 1660, 2933, 2978 cm$^{-1}$; MS (ES): 386.0 (M$^+$+1), 384.0 (M$^+$+1).

1-diisopropyloxyphosphorylmethyl-4-(3-trifluoromethylphenyl)-2-pyridone. $^1$H NMR (200 MHz, CDCl$_3$) δ1.24 (s, 3H), 1.28 (s, 3H), 1.29 (s, 3H), 1.31 (s, 3H), 4.39–4.45 (d, J=13.0 Hz, 2H), 4.64–4.78 (m, 2H), 6.40–6.45 (dd, J=2.2, 7.0 Hz, 1H), 6.76(d, J=2.0 Hz, 1H), 7.50–7.77 (m, 5H); $^{13}$C NMR (50.3 MHz, CDCl$_3$) δ23.7, 23.8, 23.9, 24.0, 41.2, 44.3, 72.1, 72.2, 105.3, 117.2, 121.1, 123.4, 123.5, 123.6, 123.7, 126.0, 126.1, 126.2, 126.3, 126.5, 128.4, 128.6 129.7, 130.0, 130.1, 130.5, 131.2, 131.8, 132.0, 132.2, 132.5, 138.1, 138.2, 150.4, 161.8; IR (film) ν989, 1124, 1241, 1337, 1597, 1663, 2935, 2981 cm$^{-1}$.

1-diisopropyloxyphosphorylmethyl-4-(3-methoxyphenyl)-2-pyridone. $^1$H NMR (200 MHz, CDCl$_3$) δ1.24 (s, 3H), 1.27 (s, 3H), 1.28 (s, 3H), 1.31 (s, 3H), 3.81 (s, 3H), 4.38–4.45 (d, J=13.2 Hz, 2H), 4.63–4.79 (m, 2H), 6.41–6.46 (dd, J=2.0, 7.2 Hz, 1H), 6.76–6.77 (d, J=2.0 Hz, 1H), 6.91–6.97 (m, 1H), 7.02–7.16 (m, 2H); 7.29–7.37 (dd, J=8.0, 8.0 Hz, 1H), 7.52–7.56 (d, J=7.2 Hz, 1H); $^{13}$C NMR (50.3 MHz, CDCl$_3$) δ23.7, 23.8, 23.9, 24.0, 41.0, 44.2, 55.3, 72.0, 72.1, 105.8, 112.3, 115.1, 116.7, 119.1, 130.1, 137.5, 138.7, 151.8, 160.1, 162.0; IR (film) ν985, 1178,.1248, 1348, 1598, 1660, 2933, 2978 cm$^{-1}$.

1-diisopropyloxyphosphorylmethyl-4-(3-thienyl)-2-pyridone. $^1$H NMR (200 MHz, CDCl$_3$) δ1.23 (s, 3H), 1.26 (s, 3H), 1.27 (s, 3H), 1.30 (s, 3H), 4.36–4.43 (d, J=12.8 Hz, 2H), 4.62–4.78 (m, 2H), 6.41–6.46 (dd, J=2.0, 7.2 Hz, 1H), 6.76–6.77 (d, J=2.0 Hz, 1H), 7.31–7.40 (m, 2H), 7.49–7.53 (d, J=7.2 Hz, 1H), 7.58–7.60 (m, 1H); $^{13}$C NMR 125.6, 127.1, 137.6, 138.6, 145.8, 162.2; IR (film) ν979, 1104, 1238, 1344, 1591, 1657, 2933, 2979 cm$^{-1}$.

1-diisopropyloxyphosphorylmethyl-4-(4-methoxyphenyl)-2-pyridone. $^1$H NMR (200 MHz, CDCl$_3$) δ1.24 (s, 3H), 1.27 (s, 3H), 1.28 (s, 3H), 1.31 (s, 3H), 3.81 (s, 3H), 4.37– 4.43 (d, J=12.8 Hz, 2H), 4.62–4.78 (m, 2H), 6.40–6.45 (dd, J=2.0, 7.4 Hz, 1H), 6.72–6.73 (d, J=2.0 Hz, 1H), 6.91–6.95 (d, J=8.6 Hz, 2H), 7.48–7.53 (m, 3H); $^{13}$C NMR (50.3 MHz, CDCl$_3$) δ23.6, 23.7, 230.8, 23.9, 41.0, 44.1, 55.3, 72.0, 72.1, 105.5, 114.4, 115.3, 128.0, 129.3, 137.3, 151.2, 161.0, 162.1; IR (film) ν978, 1178, 1241, 1349, 1595, 1656, 2933, 2978 cm$^{-1}$.

1-diisopropyloxyphosphorylmethyl-4-(2-naphthyl)-2-pyridone. $^1$H NMR (200 MHz, CDCl$_3$) δ1.28 (s, 3H), 1.30 (s, 3H), 1.31 (s, 3H), 1.34 (s, 3H), 4.43–4.49 (d, J=13.0 Hz, 2H), 4.68–4.82 (m, 2H), 6.58–6.62 (dd, J=2.0, 7.0 Hz, 1H), 6.92–6.93 (d, J=2.0 Hz, 1H), 7.49–7.69 (m, 4H), 7.80–7.93 (m, 3H), 8.05 (s, 1H); $^{13}$C NMR (50.3 MHz, CDCl$_3$) δ23.7, 23.8, 23.9, 24.0, 41.1, 44.2, 72.1, 72.2, 105.9, 117.0, 124.1, 126.5, 126.8, 127.1, 127.8, 128.6, 128.9, 133.3, 133.8, 134.5, 137.6, 151.8, 162.2; IR (film) ν988, 1104, 1239, 1386, 1591, 1658, 2932, 2979 cm$^-$.

1-diisopropyloxyphosphorylmethyl-4-(3-chloro-4-fluorophenyl)-2-pyridone. $^1$H NMR (200 MHz, CDCl$_3$) δ1.25 (s, 3H), 1.28 (s, 3H), 1.29 (s, 3H), 1.32 (s, 3H), 4.38–4.45 (d, J=13.0 Hz, 2H), 4.64–4.80 (m, 2H), 6.34–6.39 (dd, J=2.0, 7.2 Hz, 1H), 6.70–6.71 (d, J=2.0 Hz, 1H), 7.15–7.24 (dd, J=8.6, 8.6 Hz, 1H), 7.38–7.46 (m, 1H), 7.56–7.61 (m, 2H); $^{13}$C NMR(50.3 MHz, CDCl$_3$) δ23.7, 23.8, 23.9, 24.0, 41.2, 44.3, 72.1, 72.2, 105.2, 116.9, 117.0, 117.5, 121.7, 122.1, 126.6, 126.7, 127.5, 128.4, 129.1, 129.4, 130.6, 134.5, 134.6, 138.0, 138.3, 149.6, 156.4, 161.5, 161.8; IR (film) ν985, 1140, 1238, 1346, 1594, 1660, 2933, 2981 cm$^{-1}$.

1-diisopropyloxyphosphorylmethyl-4-(2,4-dichlorophenyl)-2-pyridone. $^1$H NMR (200 MHz, CDCl$_3$) δ1.24 (s, 3H), 1.27 (s, 3H), 1.28 (s, 3H), 1.31 (s, 3H), 4.38–4.46 (d, J=13.0 Hz, 2H), 4.63–4.79 (m, 2H), 6.22–6.26 (dd, J=1.8, 7.2 Hz, 1H), 6.54–6.55 (d, J=1.8 Hz, 1H), 7.18–7.30 (m, 2H), 7.43–7.54 (m, 2H); $^{13}$C NMR (50.3 MHz, CDCl$_3$) δ23.7, 23.8, 23.9, 24.0, 41.2, 44.3, 72.1, 72.2, 107.8, 120.4, 127.5, 130.1, 131.0, 132.8, 135.4, 135.8, 137.0, 149.9, 161.5; IR (film) ν985, 1142, 1240, 1348, 1596, 1661, 2933, 2979 cm$^-$.

1-diisopropyloxyphosphorylmethyl-4-(3,5-bistrifluoromethylphenyl)-2-pyridone. $^1$H NMR (200 MHz, CDCl$_3$) δ1.27 (s, 3H), 1.29 (s, 3H), 1.30 (s, 3H), 1.33 (s, 3H), 4.40–4.47 (d, J=13.0 Hz, 2H), 4.67–4.80 (m, 2H), 6.40–6.45 (dd, J=2.0, 7.2 Hz, 1H), 6.79–6.80(d, J=2.0 Hz, 1H), 7.59–7.70 (m, 2H), 7.89–7.978 (m, 2H); IR (film) ν990, 1120 1172, 1283, 1375, 1596, 1669, 2984, 3063 cm$^{-1}$.

1-diisopropyloxyphosphorylmethyl-4-(4-fluoromethylphenyl)-2-pyridone. $^1$H NMR (200 MHz, CDCl$_3$) δ1.25 (s, 3H), 1.28 (s, 3H), 1.29 (s, 3H), 1.31 (s, 3H), 4.38–4.45 (d, J=13.0 Hz, 2H), 4.67–4.80 (m, 2H), 6.38–6.42 (dd, J=1.8, 7.2 Hz, 1H), 6.71–6.72 (d, J=2.0 Hz, 1H), 7.06–7.15 (m, 2H), 7.49–7.57 (m, 3H); $^{13}$C NMR (50.3 MHz, CDCl$_3$) δ23.6, 23.7, 23.8, 23.9, 41.0, 44.2, 72.0, 72.1, 105.5, 115.8, 116.2, 116.4, 128.5, 128.8, 133.4, 137.7, 150.8, 161.9, 166.2; IR (film) ν987, 1161, 1234, 1348, 1587, 1659, 2933, 2981 cm$^{-1}$.

Example 12

1-Diisopropyloxyphosphorylmethyl-4-Phenylethynyl-2-Pyridone

A mixture of 1-diisopropyloxyphosphorylmethyl-4-trifluoromethanesulfonyloxy-2-pyridone (0.21 g, 0.50 mmol), dichlorobisa(triphenylphosphine)palladium(II) (0.007 g, 0.01 mmol), copper iodide (0.002 g, 0.01 mmol) and diisopropylethylamine (0.13 g, 0.17 mL, 1.00 mmol) in N,N-dimethylformamide (5.00 mL) was heated at 100° C. for 14 hr. After cooling down to room temperature, water and ethyl acetate was added and separated. The aqueous layer was extracted with ethyl acetate (2×) and the combined ethyl acetate solution was dried (MgSO4) and filtered. The filtrate was concentrated in vacuo to dryness. The residue was subjected to column chromatography (ethyl acetate) to give 0.18 g (96%) of 1-diisopropyloxyphosphorylmethyl-4-phenylethynyl-2-pyridone. $^1$H NMR (200 MHz, CDCl$_3$) δ1.23 (s, 3H), 1.25 (s, 3H), 1.26 (s, 3H), 1.29 (s, 3H), 4.33–4.40 (d, J=12.8 Hz, 2H), 4.61–4.77 (m, 2H), 6.20–6.25 (dd, J=1.8, 7.2 Hz, 1H), 6.69–6.70 (d, J=1.8 Hz, 1H), 7.29–7.37 (m, 3H), 7.42–7.51 (m, 3H).

The following compounds were obtained in a manner similar to that of Example 12:

1-(tert-butyloxycarbonylmethyl)-4-phenylethynyl-2-pyridone. $^1$H NMR (200 MHz, CDCl$_3$) δ1.48 (s, 9H), 4.53 (s, 2H), 6.23–6.27 (m, 1H), 6.73 (s, 1H), 7.14–7.18 (d, J=7.0 Hz, 1H), 7.33–7.40 (m, 3H), 7.50–7.55 (m, 2H); MS (ES): 310.1 (M$^+$+1), 254.0.

1-(3-methoxycarbonylpropyl-1)-4-phenylethynyl-2-pyridone 1H NMR (200 MHz, CDCl$_3$) δ2.00–2.07 (m, 2H), 2.35–2.43 (t, J=7.2 Hz, 2H), 3.68 (s, 3H), 3.94–4.01 (t, J=7.2 Hz, 2H), 6.21–6.25 (dd, J=1.8, 7.0 Hz, 1H), 6.70–6.71 (d, J=1.8 Hz, 1H), 7.22–7.25 d, J=7.0 Hz, 1H), 7.34–7.38 (m, 3H), 7.52–7.55 (m, 2H); MS (ES): 296.1 (M$^+$+1).

Example 13

To a solution of 14 (0.063 g, 0.094 mmol) in N,N-dimethylformamide (1.00 mL) was added N-methylmorpholine (0.038 g, 0.041 mL, 0.37 mmol) and acetic anhydride (0.014 g, 0.14 mmol) at 0° C. The resulted mixture was stirred at room temperature for 48 hr. After removal of the solvent, the residue was triturated with ether and filtered to give 0.04 g (71%) of the desired product 15 MS (ES): 600.3 (M$^+$+1).

Example 14

In a manner similar to that of Example 7, the following compounds were obtained:

Compound 12: MS (ES): 582.2 (M$^+$+1).

1-dihydroxyphosphorylmethyl-4-(2-methylphenyl)-2-pyridone: $^1$H NMR (200 MHz, DMOS-d$_6$) δ2.26 (s, 3H), 4.26–4.33 (d, J=12.8 Hz, 2H), 6.25–6.30 (m, 2H), 7.20–7.41 (m, 4H), 7.62–7.65 (d, J=6.8 Hz, 1H); MS (ES$^+$): 280.3 (M$^+$1).

1-dihydroxyphosphorylmethyl-4-(3-nitrophenyl)-2-pyridone: $^1$H NMR (200 MHz, CD$_3$OD) δ4.51–4.57 (d, J=13.0 Hz, 2H), 6.83–6.95 (m, 2H), 7.68–7.85 (m, 2H), 8.07–8.11 (d, J=7.6 Hz, 1H); 8.28–8.32 (d, J=7.6 Hz, 1H), 8.44 (s, 1H).

1-dihydroxyphosphorylmethyl-4-(2-methoxyphenyl)-2-pyridone: $^1$H NMR (200 MHz, DMSO-d$_6$) δ3.81 (s, 3H), 4.24–4.31 (d, J=13.8 Hz, 2H), 6.59–6.70 (m, 2H), 6.90–7.04 (m, 1H), 7.16–7.44 (m, 3H), 7.66–7.69 (d, J=7.2 Hz, 1H); MS (ES$^-$): 294.2 (M$^+$–1).

1-dihydroxyphosphorylmethyl-4-(2-trifluoromethylphenyl)-2-pyridone: $^1$H NMR (200 MHz, CD$_3$OD) δ4.56–4.62 (d, J=12.6 Hz, 2H), 6.47–6.59 (m, 2H), 7.39–7.43 (d, J=7.2 Hz, 1H), 7.54–7.83 (m, 4H); MS (ES$^-$): 332.1 (M$^+$–1).

1-dihydroxyphosphorylmethyl-4-(3-chlorophenyl)-2-pyridone: $^1$H NMR (200 MHz, CD$_3$OD) δ4.59–4.65 (d, J=12.6 Hz, 2H), 6.86–6.99 (m, 2H), 7.41–7.79(m, 5H); MS (ES$^+$): 302.2 (M$^+$+1), 300.2 (M$^+$+1).

1-dihydroxyphosphorylmethyl-4-(3-trifluoromethylphenyl)-2-pyridone: H NMR (200 MHz, CD$_3$OD) δ4.49–4.55 (d, J=13.0 Hz, 2H), 6.71–6.75 (dd, J=2.0, 7.0 Hz, 1H), 6.83–6.84 (d, J=2.0 Hz, 1H), 7.69–7.81 (m, 3H), 7.91 (br, 2H); MS (ES$^-$): 332.0 (M$^+$–1).

1-dihydroxyphosphorylmethyl-4-(3-methoxyhenyl)-2-pyridone: $^1$H NMR (200 MHz, CD$_3$OD) δMS (ES$^-$): 294.2 (M$^+$–1).

1-dihydroxyphosphorylmethyl-4-(3-thienyl)-2-pyridone: $^1$H NMR (200 MHz, DMSO-d$_6$) δ4.23–4.29 (d, J=13.0 Hz, 2H), 6.65–6.81 (m, 2H), 7.58–7.68 (m, 3H), 8.13 (s, 1H); MS (ES$^-$): 270.2 (M$^+$–1).

1-dihydroxyphosphorylmethyl-4-(2-naphthyl)-2-pyridone: $^1$H NMR (200 MHz, DMSO-d$_6$) δ4.29–4.35 (d, J=11.8 Hz, 2H), 6.77–6.81 (d, J=7.4 Hz, 1H), 6.85 (s, 1H), 7.49 (br, 2H), 7.72–7.76 (d, J=7.4 Hz, 1H), 7.82–8.04 (m, 4H), 8.34 (s, 1H); MS (ES$^-$): 314.2 (M$^+$–1).

1-dihydroxyphosphorylmethyl-4-(3-chloro-4-fluorophenyl)-2-pyridone: $^1$H NMR (200 MHz, DMSO-d$_6$) δ4.26–4.32 (d, J=12.6 Hz, 2H), 6:62–6.60 (d, J=7.2 Hz, 1H), 6.75 (s, 1H), 7.46–7.80 (m, 3H), 7.95–7.99 (d, J=7.0 Hz, 1H); MS (ES$^-$): 316.1 (M$^+$–1).

1-dihydroxyphosphorylmethyl-4-(2,4-dichlorophenyl)-2-pyridone: $^1$H NMR (200 MHz, CD$_3$OD) δ4.27–4.33 (d, J=13.2 Hz, 2H), 6.30–6.34 (d, J=7.0 Hz, 1H), 6.42 (s, 1H), 7.42–7.55 (m, 2H), 7.65–7.69 (d, J=7.0 Hz, 1H), 7.75 (s, 1H);

1-dihydroxyphosphorylmethyl-4-(3,5-bistrifluoromethylphenyl)-2-pyridone: $^1$H NMR (200 MHz, CD$_3$OD) δ4.49–4.56 (d, J=13.4 Hz, 2H), 6.77–6.81 (dd, J=2.0, 7.2 Hz, 1H), 6.89–6.90 (d, J=2.0 Hz, 1H), 7.81–7.84 (d, J=7.2 Hz, 1H), 8.08 (br, 1H); 8.25 (br, 2H); MS (ES$^+$): 402.1 (M$^+$+1), 1-dihydroxyphosphorylmethyl-4-(4-fluorophenyl)-2-pyridone: $^1$H NMR (200 MHz, DMOS-d$_6$) δ4.21–4.27 (d, J=13.4 Hz, 2H), 6.58–6.62 (d, J=7.0 Hz, 1H), 6.70 (s, 1H), 7.22–7.35 (m, 2H), 7.60–7.80 (m, 3H); MS (ES$^-$): 282.2 (M$^+$–1).

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound represented by the formula (Formula I):

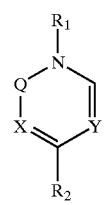

in which

X and Y, each independently, are CH;

Q is C(O);

R$_1$ is CHZ$_1$Z$_2$, wherein Z$_1$ and Z$_2$ are each independently, a hydrogen atom, PO$_3$H$_2$, or SO$_3$H, provided that both Z$_1$ and Z$_2$ are not both hydrogen atoms, or CH(OH)Z$_1$ or CHFZ$_1$, provided Z$_1$ is not a hydrogen atom; and R$_2$ is a substituted or unsubstituted alkyl, aryl, or alkylaryl moiety or a salt or ester thereof.

2. The compound of claim 1, wherein R$_2$ is an aryl moiety.

3. The compound of claim 1, wherein R$_2$ is a methylene group having attached thereto a substituted or unsubstituted amino acid, a peptide, amine, carbamate, or sulfonamide.

4. The compound of claim 1, wherein R$_2$ is CH$_2$NR$_3$R$_4$, wherein R$_3$ and R$_4$ are each independently a hydrogen atom or a substituted or unsubstituted alkyl, aryl, or alkylaryl moiety or together form a substituted or unsubstituted heterocyclic ring, or are each independently C(O)R$_5$, SO$_2$R$_5$, or SO$_2$N(R$_5$)$_2$, wherein R$_5$ is a hydrogen atom or a substituted or unsubstituted alkyl, aryl, or alkylaryl moiety.

5. The compound of claim 1, wherein R$_2$ is an ethylene group having attached thereto a substituted or unsubstituted amino acid, a peptide, amine, carbamate, or sulfonamide.

6. The compound of claim 1, wherein R$_2$ is CH$_2$CH (COR$_6$)NR$_3$R$_4$, wherein R$_3$ and R$_4$ are each independently a hydrogen atom or a substituted or unsubstituted alkyl, aryl, or alkylaryl moiety or together form a substituted or unsubstituted heterocyclic ring, or are each independently C(O)R$_5$, SO$_2$R$_5$ or SO$_2$N(R$_5$)$_2$ wherein R$_5$ is a hydrogen atom or a substituted or unsubstituted alkyl, aryl, or alkylaryl moiety and wherein R$_6$ is an amino acid residue, a peptide, or a substituted or unsubstituted alkyl, aryl, or alkylaryl moiety.

7. A pharmaceutical composition for inhibiting a protein-protein interaction mediated by a SH2 domain or a tyrosine phosphatase in a mammal, comprising a therapeutically effective amount of a compound represented by the formula (Formula I):

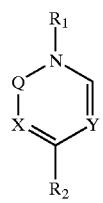

(I)

in which

X and Y, each independently, are CH;

Q is C(O);

$R_1$ is $CHZ_1Z_2$, wherein $Z_1$ and $Z_2$ are each independently, a hydrogen atom, $PO_3H_2$, or $SO_3H$, provided that both $Z_1$ and $Z_2$ are not both hydrogen atoms, or $CH(OH)Z_1$ or $CHFZ_1$, provided $Z_1$ is not a hydrogen atom; and $R_2$ is a substituted or unsubstituted alkyl, aryl, or alkylaryl moiety or a salt or ester thereof.

8. The pharmaceutical composition of claim 7, wherein $R_2$ is an aryl moiety.

9. The pharmaceutical composition of claim 7, wherein $R_2$ is a methylene group having attached thereto a substituted or unsubstituted amino acid, a peptide, amine, carbamate, or sulfonamide.

10. The pharmaceutical composition of claim 7, wherein $R_2$ is $CH_2NR_3R_4$, wherein $R_3$ and $R_4$ are each independently a hydrogen atom or a substituted or unsubstituted alkyl, aryl, or alkylaryl moiety or together form a substituted or unsubstituted heterocyclic ring, or are each independently $C(O)R_5$, $SO_2R_5$, or $SO_2N(R_5)_2$ wherein $R_5$ is a hydrogen atom or a substituted or unsubstituted alkyl, aryl, or alkylaryl moiety.

11. The pharmaceutical composition of claim 7, wherein $R_2$ is an ethylene group having attached thereto a substituted or unsubstituted amino acid, a peptide, amine, carbamate, or sulfonamide.

12. The pharmaceutical composition of claim 7, wherein $R_3$ is $CH_2CH(COR_6)NR_3R_4$, wherein $R_3$ and $R_4$ are each independently a hydrogen atom or a substituted or unsubstituted alkyl, aryl, or alkylaryl moiety or together form a substituted or unsubstituted heterocyclic ring, or are each independently $C(O)R_5$, $SO_2R_5$ or $SO_2N(R_5)_2$ wherein $R_5$ is a hydrogen atom or a substituted or unsubstituted alkyl, aryl, or alkylaryl moiety and wherein $R_6$ is an amino acid residue, a peptide, or a substituted or unsubstituted alkyl, aryl, or alkylaryl moiety.

13. A method for the preparation of,

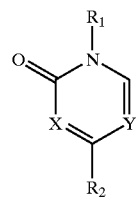

comprising the step of:
treating

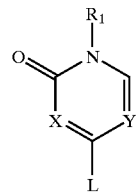

with an alkyl, aryl or alkylaryl alkylating reagent in the presence of a palladium catalyst, to provide

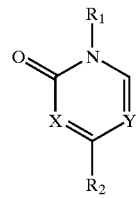

wherein
L is a leaving group and
wherein
X and Y, each independently, are CH;
$R_1$ is $CH_1Z_2$, wherein $Z_1$ and $Z_2$ are each independently, a hydrogen atom, COOH, $PO_3H_2$, or $SO_3H$, provided that both $Z_1$ and $Z_2$ are not both hydrogen atoms, or $CH(OH)Z_1$ or $CHFZ_1$, provided $Z_1$ is not a hydrogen atom; and
$R_2$ is a substituted or unsubstituted alkyl, aryl, or alkylaryl moiety or a salt or ester thereof.

14. The method of claim 13, wherein said leaving group is a triflate.

15. The method of claim 13 wherein said palladium catalyst is $Pd(PPh_3)_4$.

* * * * *